(12) United States Patent
Jung et al.

(10) Patent No.: US 9,591,121 B2
(45) Date of Patent: Mar. 7, 2017

(54) FUNCTION CONTROLLING METHOD AND ELECTRONIC DEVICE SUPPORTING THE SAME

(71) Applicant: Samsung Electronics Co., Ltd., Gyeonggi-do (KR)

(72) Inventors: Chung Hyo Jung, Gyeonggi-do (KR); Jong Gwang Jang, Gyeonggi-do (KR); Se Young Jang, Gyeonggi-do (KR); Chang Eop Kwak, Gyeonggi-do (KR); Min Su Kim, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 14/835,994

(22) Filed: Aug. 26, 2015

(65) Prior Publication Data
US 2016/0065723 A1 Mar. 3, 2016

(30) Foreign Application Priority Data
Aug. 28, 2014 (KR) .................. 10-2014-0113259

(51) Int. Cl.

| | |
|---|---|
| G08B 17/00 | (2006.01) |
| H04M 1/725 | (2006.01) |
| G06F 1/16 | (2006.01) |
| G06F 19/00 | (2011.01) |
| G06F 3/0484 | (2013.01) |
| G06F 1/20 | (2006.01) |
| G06F 1/32 | (2006.01) |
| G08B 21/18 | (2006.01) |
| H04W 52/02 | (2009.01) |

(52) U.S. Cl.
CPC ...... *H04M 1/72569* (2013.01); *G06F 1/1626* (2013.01); *G06F 1/206* (2013.01); *G06F 1/3206* (2013.01); *G06F 3/0484* (2013.01); *G06F 19/3406* (2013.01); *G08B 21/182* (2013.01); *H04M 1/72583* (2013.01); *H04W 52/029* (2013.01); *H04W 52/0251* (2013.01); *H04W 52/0267* (2013.01); *H04W 52/0274* (2013.01)

(58) Field of Classification Search
CPC ... G06F 1/1626; G06F 3/0484; G06F 19/3406
USPC ............................ 340/586; 700/17; 715/771
See application file for complete search history.

(56) References Cited

U.S. PATENT DOCUMENTS

| | | | |
|---|---|---|---|
| 6,507,820 | B1 | 1/2003 | Deutgen |
| 6,539,355 | B1 | 3/2003 | Omori et al. |
| 7,340,379 | B2 | 3/2008 | Kunkel et al. |
| 7,676,043 | B1 | 3/2010 | Tsutsui et al. |
| 7,715,573 | B1 | 5/2010 | Yonemoto et al. |

(Continued)

FOREIGN PATENT DOCUMENTS

KR  1999-0082929 A  11/1999

*Primary Examiner* — John A Tweel, Jr.
(74) *Attorney, Agent, or Firm* — Cha & Reiter, LLC

(57) ABSTRACT

An electronic device includes: a communication interface configured to support a communication function; and one or more processors configured to perform a temperature detection of the electronic device during the communication function execution, drive a timer warning a communication function termination if the detected temperature information satisfies a specified temperature condition, and output count information corresponding to the timer driving.

24 Claims, 13 Drawing Sheets

(56) References Cited

U.S. PATENT DOCUMENTS

| | | |
|---|---|---|
| 7,813,931 B2 | 10/2010 | Hetherington et al. |
| 8,036,394 B1 | 10/2011 | Yonemoto et al. |
| 8,121,847 B2 | 2/2012 | Klinke et al. |
| 8,296,686 B1 * | 10/2012 | Tedesco ............. G06F 19/3406 715/865 |
| 8,311,842 B2 | 11/2012 | Song et al. |
| 8,396,716 B2 | 3/2013 | Qi et al. |
| 8,560,304 B2 | 10/2013 | Choo et al. |
| 8,560,329 B2 | 10/2013 | Qi et al. |
| 8,644,960 B2 * | 2/2014 | Laflamme ............ G06F 1/1626 700/17 |
| 8,712,768 B2 | 4/2014 | Laaksonen et al. |
| 9,122,430 B1 * | 9/2015 | Tedesco ............. G06F 19/3406 |
| 2004/0064324 A1 | 4/2004 | Graumann |
| 2004/0138876 A1 | 7/2004 | Kallio et al. |
| 2005/0267741 A1 | 12/2005 | Laaksonen et al. |
| 2006/0111150 A1 | 5/2006 | Klinke et al. |
| 2006/0187032 A1 | 8/2006 | Kunkel et al. |
| 2006/0247922 A1 | 11/2006 | Hetherington et al. |
| 2008/0004866 A1 | 1/2008 | Virolainen et al. |
| 2008/0108331 A1 | 5/2008 | Jin et al. |
| 2008/0188965 A1 | 8/2008 | Bruey |
| 2008/0215344 A1 | 9/2008 | Song et al. |
| 2008/0270125 A1 | 10/2008 | Choo et al. |
| 2010/0144308 A1 | 6/2010 | Jin et al. |
| 2010/0169086 A1 | 7/2010 | Qi et al. |
| 2011/0230163 A1 | 9/2011 | Jin et al. |
| 2012/0094714 A1 | 4/2012 | Yoshikawa |
| 2012/0282882 A1 | 11/2012 | Jin et al. |
| 2013/0117030 A1 | 5/2013 | Qi et al. |
| 2013/0230057 A1 | 9/2013 | Hori et al. |
| 2013/0242858 A1 | 9/2013 | Amine |
| 2013/0244610 A1 | 9/2013 | Jin et al. |
| 2014/0108986 A1 * | 4/2014 | Laflamme ............ G06F 1/1626 715/771 |
| 2014/0191873 A1 | 7/2014 | Kreiner et al. |
| 2014/0248850 A1 | 9/2014 | Jin et al. |
| 2015/0094126 A1 | 4/2015 | Kreiner et al. |

\* cited by examiner

US 9,591,121 B2

FUNCTION CONTROLLING METHOD AND ELECTRONIC DEVICE SUPPORTING THE SAME

CLAIM OF PRIORITY

This application claims the benefit under 35 U.S.C. §119(a) of a Korean patent application filed on Aug. 28, 2014 in the Korean Intellectual Property Office and assigned Serial number 10-2014-0113259, the entire disclosure of which is hereby incorporated by reference for all purposes.

TECHNICAL FIELD

The present disclosure relates to a function control of an electronic device.

BACKGROUND

An electronic device such as a smartphone may provide various user functions. Such an electronic device may provide a user function by using power such as a battery.

The above-mentioned electronic device may cause heat generation due to the power use. The heat generation may be increased in relation to a function management of an electronic device. For example, an electronic device using a communication function may cause heat generation more in comparison to an electronic device not using a communication function. Such heat generation may damage the hardware of an electronic device or affect a user.

SUMMARY

Accordingly, an aspect of the present disclosure is to provide a function controlling method for reducing hardware failure or user damage by limiting a function management and an electronic device for supporting the same.

In accordance with an aspect of the present disclosure, an electronic device includes: a communication interface configured to support a communication function; and one or more processors configured to perform a temperature detection of the electronic device during a communication function execution, drive a timer to warn of a communication function termination if a detected temperature satisfies a specified temperature condition, and output count information corresponding to the timer driving.

In accordance with another aspect of the present disclosure, provided is a function controlling method of an electronic device. The method includes: performing a temperature detection of the electronic device corresponding to a communication function execution; driving a timer to warn of a communication function termination if the detected temperature information satisfies a specified temperature condition; and outputting count information corresponding to the timer driving.

In accordance with another aspect of the present disclosure an electronic device comprises a processor. The processor comprises a communication processor and an application processor. The communication processor is configured to detect a temperature, and establish a phone call. The application processor is configured to perform one of cause the electronic device to enter a cool down mode, or issue a warning message in response to at least one particular interrupt from the communication processor. The communication processor sends the at least one particular interrupt to the application processor, responsive to detecting the temperature exceeds one or more thresholds.

DETAILED DESCRIPTION

Figure 1:
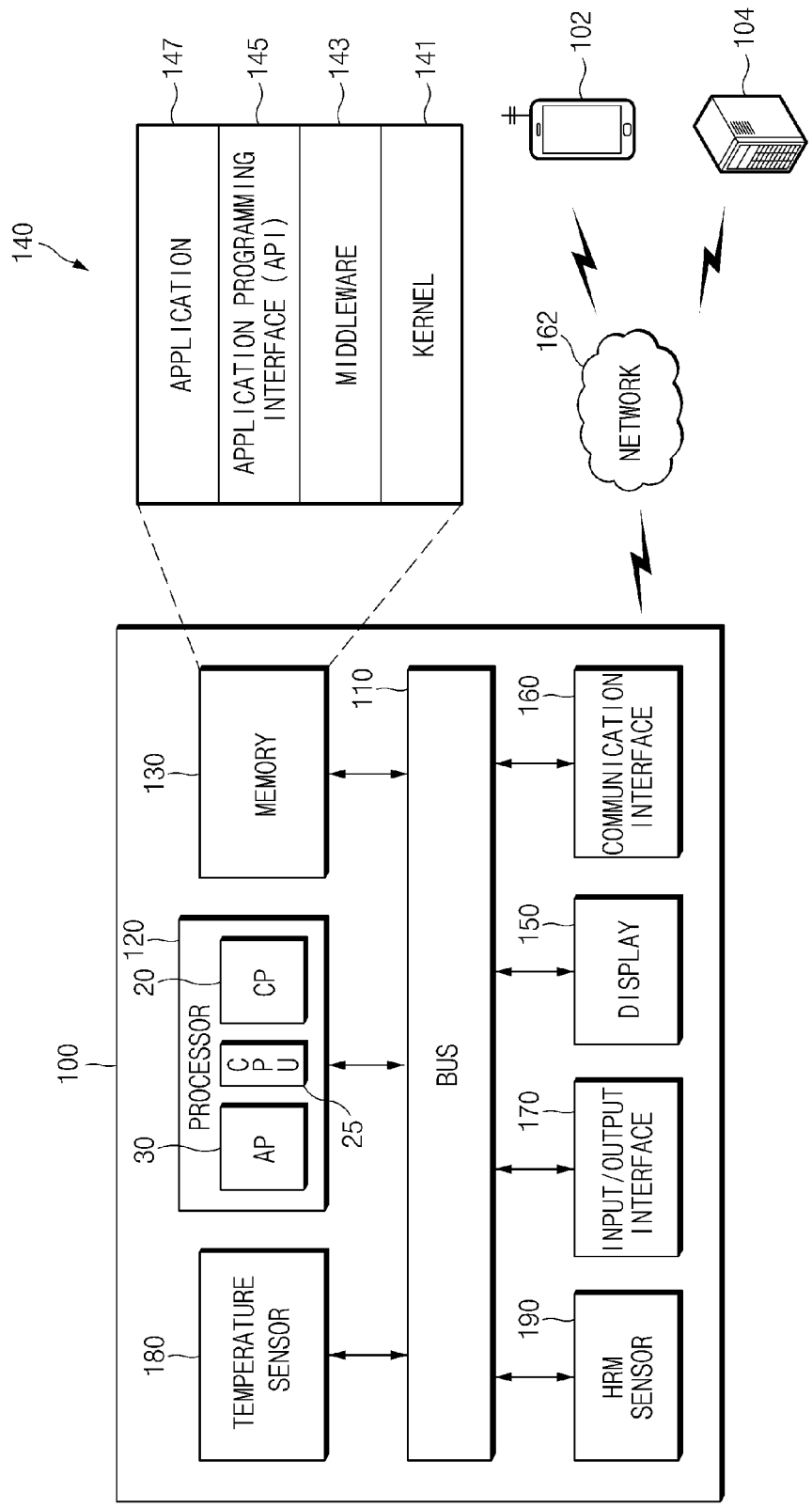
FIG. 1 is a view illustrating an electronic device management environment according to various embodiments of the present disclosure.

Hereinafter, various embodiments of the present disclosure are disclosed with reference to the accompanying drawings. However, this does not limit various embodiments of the present disclosure to a specific embodiment and it should be understood that the present disclosure covers all the modifications, equivalents, and/or alternatives of this disclosure provided they come within the scope of the appended claims and their equivalents. With respect to the descriptions of the drawings, like reference numerals refer to like elements.

The term "include," "comprise," and "have", or "may include," or "may comprise" and "may have" used herein indicates disclosed functions, operations, or existence of elements but does not exclude other functions, operations or elements.

For instance, the expression "A or B", or "at least one of A or/and B" may indicate include A, B, or both A and B. For instance, the expression "A or B", or "at least one of A or/and B" may indicate (1) at least one A, (2) at least one B, or (3) both at least one A and at least one B.

The terms such as "1st", "2nd", "first", "second", and the like used herein may refer to modifying various different elements of various embodiments of the present disclosure, but do not limit the elements. The expressions may be used to distinguish one element from another element. For instance, "a first user device" and "a second user device" may indicate different users regardless of the order or the importance. For example, a first component may be referred to as a second component and vice versa without departing from the scope of the present disclosure.

In various embodiments of the present disclosure, it will be understood that when a component (for example, a first component) is referred to as being "(operatively or communicatively) coupled with/to" or "connected to" another component (for example, a second component), the component can be directly connected to the other component or connected through another component (for example, a third component). In various embodiments of the present disclosure, it will be understood that when a component (for example, a first component) is referred to as being "directly connected to" or "directly access" another component (for example, a second component), another component (for example, a third component) does not exist between the component (for example, the first component) and the other component (for example, the second component).

The expression "configured to" used in various embodiments of the present disclosure may be interchangeably used with "suitable for", "having the capacity to", "designed to", "adapted to", "made to", or "capable of" according to a situation, for example. The term "configured to" may not necessarily mean "specifically designed to" in terms of hardware. Instead, the expression "a device configured to" in some situations may mean that the device and another device or part are "capable of". For example, "a processor configured to perform A, B, and C" in a phrase may mean a dedicated processor (for example, an embedded processor) for performing a corresponding operation or a generic-purpose processor (for example, a CPU or application processor) for performing corresponding operations by executing at least one software program stored in a memory device.

Terms used in various embodiments of the present disclosure are used to describe specific embodiments of the present disclosure, and are not intended to limit the scope of other embodiments. The terms of a singular form may include plural forms unless they have a clearly different meaning in the context. Otherwise indicated herein, all the terms used herein, which include technical or scientific terms, may have the same meaning that is generally understood by a person skilled in the art. In general, the terms defined in the dictionary should be considered to have the same meaning as the contextual meaning of the related art, and, unless clearly defined herein, should not be understood abnormally or as having an excessively formal meaning. In any cases, even the terms defined in this specification cannot be interpreted as excluding embodiments of the present disclosure.

According to various embodiments of the present disclosure, electronic devices may include at least one of smartphones, tablet personal computers (PCs), mobile phones, video phones, electronic book (e-book) readers, desktop personal computers (PCs), laptop personal computers (PCs), netbook computers, workstation server, personal digital assistants (PDAs), portable multimedia player (PMPs), MP3 players, mobile medical devices, cameras, and wearable devices (for example, smart glasses, head-mounted-devices (HMDs), electronic apparel, electronic bracelets, electronic necklaces, electronic accessories, electronic tattoos, smart mirrors, and smart watches).

According to some embodiments of the present disclosure, an electronic device may be smart home appliances. The smart home appliances may include at least one of, for example, televisions, digital video disk (DVD) players, audios, refrigerators, air conditioners, cleaners, ovens, microwave ovens, washing machines, air cleaners, set-top boxes, home automation control panels, security control panels, TV boxes (e.g., Samsung HomeSync™, Apple TV™ or Google TV™), game consoles (for example, Xbox™ and PlayStation™), electronic dictionaries, electronic keys, camcorders, and electronic picture frames.

According to some embodiments of the present disclosure, an electronic device may include at least one of various medical devices supporting call forwarding service (for example, various portable measurement devices (for example, glucometers, heart rate meters, blood pressure meters, temperature meters, etc.), magnetic resonance angiography (MRA) devices, magnetic resonance imaging (MRI) devices, computed tomography (CT) devices, medical imaging devices, ultrasonic devices, etc.), navigation devices, global positioning system (GPS) receivers, event data recorders (EDRs), flight data recorders (FDRs), vehicle infotainment devices, marine electronic equipment (for example, marine navigation systems, gyro compasses, etc.), avionics, security equipment, vehicle head units, industrial or household robots, financial institutions' automatic teller's machines (ATMs), or stores' point of sales (POS) or internet of things (for example, bulbs, various sensors, electric or gas meters, sprinkler systems, fire alarms, thermostats, street lights, toasters, exercise equipment, hot water tanks, heaters, boilers, etc.).

In various embodiments of the present disclosure, an electronic device may include at least one of part of furniture or buildings/structures supporting call forwarding service, electronic boards, electronic signature receiving devices, projectors, and various measuring instruments (for example, water, electricity, gas, or radio signal measuring instruments). An electronic device according to various embodiments of the present disclosure may be one of the above-mentioned various devices or a combination thereof. Additionally, an electronic device according to an embodiment of the present disclosure may be a flexible electronic device. Additionally, an electronic device according to an embodiment of the present disclosure is not limited to the above-mentioned devices and may include a new kind of an electronic device according to the technology development.

Hereinafter, an electronic device according to various embodiments of the present disclosure will be described in more detail with reference to the accompanying drawings. The term "user" in this disclosure may refer to a person using an electronic device or a device using an electronic device (for example, an artificial intelligent electronic device). FIG. 1 is a view illustrating an electronic device management environment according to various embodiments of the present disclosure. The electronic device management environment may include an electronic device 100, a network 162, another electronic device 102, and a server device 104.

In the electronic device management environment, the electronic device 100 may establish a communication channel with the other electronic device 102 through the network 162. Alternatively, the electronic device 100 may establish a communication channel with the server device 104. During this operation, the electronic device 100 may operate a communication channel operation related processor (for example, at least one of an application processor and a communication processor). A processor may generate a specific heat while receiving and managing a power necessary for a communication channel management. According to various embodiments of the present disclosure, the electronic device 100 may perform a temperature detection relating to a management of a processor, and may limit a function executed by a processor when the detected temperature information satisfies a specified temperature condition. According to an embodiment of the present disclosure, when the detected temperature information satisfies a specified condition, the electronic device 100, for example, may provide a function termination schedule time of a corresponding function. A user may check which time point a function that the user uses currently is terminated through a function termination schedule time check and may perform processing (for example, a manipulation for a function control of an electronic device) according thereto.

The network 162 may include telecommunications network, for example, at least one of computer network (for example, LAN or WAN), internet, and telephone network. The network 162 may support a communication channel establishment relating to communication service management of the electronic device 100. The electronic device 100 may establish a voice call channel or a video call channel with the other electronic device 102 through the network 162. According to an embodiment of the present disclosure, the electronic device 100 may establish a data communication channel with the server device 104 through the network 162. The electronic device 100 may limit at least one function in execution in correspondence to detected temperature information during a communication function management.

The other electronic device 102 may be the same or different type of the electronic device 100. The other electronic device 102 may transmit a call (for example, a voice call or a video call) connection request message to the electronic device 100 via the network 162 or may establish a communication channel to request message transmission. According to various embodiments of the present disclosure, the other electronic device 102 may receive information from the electronic device 100 at a function termination schedule time. The other electronic device 102 may output a function termination schedule time in a guide sound format or as text or image information. When a function termination schedule time elapses, the other electronic device 102 may receive communication function termination related information (for example, a communication channel release request) from the electronic device 100 and may release a communication channel.

The server device 104 may include a group of one or more servers. According to various embodiments of the present disclosure, all or part of operations executed on the electronic device 100 may be executed on another one or more electronic devices (for example, the electronic device 102 or the server device 104). The server device 104 may establish a communication channel with the electronic device 100 or the other electronic device 102 in relation to communication service support. According to an embodiment of the present disclosure, the server device 104 may receive information on a function termination schedule time from the electronic device 102. Alternatively, the server device 104 may receive a communication channel release request in correspondence to a function termination schedule time arrival. When a function termination schedule time arrives from the electronic device 100, the server device 104 may process a communication channel release at a corresponding time. Alternatively, when receiving a communication channel release request, the server device 104 may process a communication channel release.

According to an embodiment of the present disclosure, when the electronic device 100 performs a certain function or service automatically or by a request, it may request at least part of a function relating thereto from another device (for example, the other electronic device 102 or the server device 104) instead of or in addition to executing the function or service by itself. The other electronic devices (for example, the other electronic device 102 or the server device 104) may execute the requested function or an additional function and may deliver an execution result to the electronic device 100. The electronic device 100 may provide the requested function or service by processing the received result as it is or additionally. For this, for example, cloud computing, distributed computing, or client-server computing technology may be used. The electronic device 100 may include a bus 110, a processor 120, a memory 130, an input/output interface 170, a display 150, a communication interface 160, a temperature sensor 180 (for example, a thermistor), and a heart rate monitor (HRM) sensor 190. According to an embodiment of the present disclosure, the electronic device 100 may omit at least one of the components or may additionally include a different component. Additionally/alternately, although it is shown that the temperature sensor 180 is connected to the processor 120 through the bus 110, according to various embodiments of the present disclosure, the temperature sensor 180 may be directly connected to the processor 120. Alternatively, each temperature sensor may be directly connected to the application processor 30 or the communication processor 20.

The bus 110 of the electronic device 100, for example, may include a circuit for connecting the above-mentioned components 120 to 170 to each other and delivering a communication (for example, a control message and/or data) between the components. For example, the bus 110 may deliver a user function execution related input event to the processor 120. According to an embodiment of the present disclosure, the bus 110 may deliver information received from the communication interface 160 to the processor 120 and may deliver it to the input/output interface 170 or the display 150 in correspondence to a control of the processor 120. According to an embodiment of the present disclosure, the bus 110 may deliver audio data or display data (for example, including at least one of text and image) corresponding to a function termination schedule time to the input/output interface 170 or the display 150.

The processor 120 may include at least one of a communication processor (CP) 20, a central processing unit (CPU) 25, and an application processor (AP) 30. The processor 120, for example, may execute calculation or data processing for control and/or communication of at least one another component of the electronic device 100. According to various embodiments of the present disclosure, the processor 120 may perform data processing or control signal processing relating to at least one application execution. According to an embodiment of the present disclosure, the processor 120 may perform calculation processing relating to the management of a program module 140 loaded into the memory 130. For example, the processor 120 may support a virtual content playback related calculation, processing relating to a communication event reception during virtual content playback, call connection processing corresponding to a call connection request, and so on.

The application processor 30 may perform hardware control and software control relating to a user function management of the electronic device 100. For example, the application processor 30 may receive temperature information from the communication processor 20. The application processor 30 may control a function termination schedule by checking the received temperature information and a specified temperature condition. Alternatively, the application processor 30 may control a function termination schedule on the basis of a comparison of temperature information received from the temperature sensor 180 and a specified temperature condition. In relation to the function termination schedule, when a specified first temperature condition (for example, when a constrained temperature is more than 38° C./100.4° F. or 40° C./104° F.) is satisfied, the application processor 30 may perform a control to output a function termination schedule time (for example, a time for warning (or announcing, or noticing) the termination of at least one function during execution after a specific time elapses). For example, the application processor 30 may output audio data corresponding to a function termination schedule time through the input/output interface 170. Alternatively, the application processor 30 may perform a control to output display data corresponding to a function termination schedule time through the display 150. When a function termination schedule time arrives after the function termination schedule time output, the application processor 30 may terminate a corresponding function.

According to various embodiments of the present disclosure, the application processor 30 may re-perform a temperature detection after the function termination schedule time. When temperature information of a re-performance time point satisfies a specified first temperature condition, the application processor 30 may perform a function termination. When the temperature information of the re-performance time point satisfies a second temperature condition (for example, a situation of more than a limited temperature, for example, 42° C./107.6° F.), the application processor 30 may perform the processing of cool down (for example, a setting for limiting the usage of specified functions). According to various embodiments of the present disclosure, when temperature information detected after a function termination schedule time elapses satisfies a third temperature condition (for example, a situation of more than a restricted temperature, for example, 46° C./114.8° F.), the application processor 30 may control power off of the electronic device 100.

According to various embodiments of the present disclosure, the application processor 30 may guarantee a specified basic communication performance time in consideration of the efficiency of a given specific function, for example, a communication function. For example, when a communication function is executed, the application processor 30 may provide a basic communication performance time such as several minutes or several seconds, and may perform a temperature detection after the basic communication performance time elapses. The application processor 30 may process at least one of the above-mentioned function termination schedule time output, function termination, cool down, and power off in correspondence to temperature information detected after the basic communication performance time elapses.

The communication processor 20 may collect temperature information from the temperature sensor 180 and may deliver the collected temperature information to the application processor 30 in a specific period or in correspondence to a request of the application processor 30. When a function termination instruction is received from the application processor 30, the communication processor 20 may perform a control to terminate a communication function in execution. For example, the communication processor 20 may receive a communication function termination instruction from the application processor 30 at an elapse time point of a function termination schedule time. The communication processor 20 may terminate a communication function in execution and release a communication channel.

According to various embodiments of the present disclosure, the communication processor 20 may detect a temperature through the temperature sensor 180 in a specific period or a specific period. When the detected temperature information satisfies a specified temperature condition, the communication processor 20 may control an output of a function termination schedule time. The communication processor 20 may terminate a communication function after a function termination schedule time elapses. According to various embodiments of the present disclosure, the communication processor 20 may process a communication function limitation corresponding to the detected temperature information without waking up the application processor 30 in a sleep state.

The memory 130 may include volatile and/or nonvolatile memory. The memory 130, for example, may store instructions or data relating to at least one another component of the electronic device 100. The memory 130 may store software and/or programs. The programs may include a kernel 141, a middleware 143, an application programming interface (API) 145, and/or an application program (or an application) 147. At least part of the kernel 141, the middleware 143, or the API 145 may be called an operating system (OS).

According to an embodiment of the present disclosure, the memory 130 may include temperature setting information. The temperature setting information may include information such as a first temperature condition, a second temperature condition, and a third temperature condition and information defining function processing of the processor 120 in a corresponding temperature condition. The temperature setting information may be provided to a corresponding processor when the application processor 30 or the communication processor 20 is activated.

The kernel 141, for example, may control or manage system resources (for example, the bus 110, the processor 120, the memory 130, and so on) used for performing operations or functions implemented in other programs (for example, the middleware 143, the API 145, or the application program 147). Additionally, the kernel 141 may provide an interface for controlling or managing system resources by accessing an individual component of the electronic device 100 from the middleware 143, the API 145, or the application program 147. According to an embodiment of the present disclosure, the kernel 141 may provide an interface relating to a control of resources (which are necessary for at least one of a temperature information collection through a control the temperature sensor 180, a temperature information and temperature condition comparison, an output of a function termination schedule time corresponding to a comparison result, a function termination corresponding to the arrival of a function termination schedule time, cool down corresponding to the detected temperature information, and power off processing) and a hardware or software management.

The middleware 143, for example, may serve as an intermediary role for exchanging data as the API 145 or the application program 147 communicates with the kernel 141. Additionally, in relation to job requests received from the application program 147, the middleware 143, for example, may perform a control (for example, scheduling or load balancing) for the job requests by using a method of assigning a priority for using a system resource (for example, the bus 110, the processor 120, the memory 130, and so on) of the electronic device 100 to at least one application program among the application programs 147. For example, the middleware 143 may support a job assignment and assigned job processing relating to a temperature detection control of the temperature sensor 180 during a communication function execution, a comparison control of temperature information, an output of a function termination schedule time corresponding to whether a temperature condition is satisfied, a function termination, cool down, and power off.

The API 145, as an interface for allowing the application 147 to control a function provided from the kernel 131 or the middleware 132, may include at least one interface or function (for example, an instruction) for file control, window control, image processing, or character control. According to an embodiment of the present disclosure, the API 145 may include an API relating to a temperature detection of the temperature sensor 180 during communication function management, an API relating to a comparison of detected temperature information and a temperature condition, and an API relating to processing corresponding to a comparison result.

The application 147 may include various applications supported by the electronic device 100. For example, the application 147 may include a data communication related web surfing function application, a call function application, a content streaming application, and a voice search function application. According to the execution of the application 147, the electronic device 100 may support a user function. Accordingly, at least one function provided by the application 147 may be limited in correspondence to a control of the application processor 30 or the communication processor 20. According to an embodiment of the present disclosure, a communication function provided by a communication function application may maintain an execution state or may be terminated after a function termination schedule time elapses corresponding to a comparison of detected temperature information and a specified temperature condition.

The input/output interface 170, for example, may serve as an interface for delivering instructions or data inputted from a user or another external device to another component(s) of the electronic device 100. Additionally, the input/output interface 170 may output instructions or data received from another component(s) of the electronic device 100 to a user or another external device.

According to an embodiment of the present disclosure, the input/output interface 170 may include an audio processing module having a speaker and a mike. The audio processing module may collect a call sound or output a received call sound corresponding to a call function performance. According to an embodiment of the present disclosure, the input/output interface 170 may output audio data corresponding to a function termination schedule time through the speaker in correspondence to a control of the processor 120. For example, the input/output interface 170 may output audio data for counting a specific time. According to various embodiments of the present disclosure, the input/output interface 170 may output a specified alarm message corresponding to a comparison of detected temperature information and specified temperature condition. According to various embodiments of the present disclosure, the input/output interface 170 may output guide information on a cool down state. For example, when an input event relating to the execution of a specified function (for example, a communication function) occurs in a state that a specified temperature condition is satisfied (a situation of more than a specified restricted temperature), the input/output interface 170 may output audio data for guiding a cool down state in which a corresponding function execution is impossible. According to various embodiments of the present disclosure, when it is more than a specified temperature condition (for example, more than a restricted temperature) in correspondence to a change of detected temperature information, the input/output interface 170 may perform a guide sound output for a cool down state.

The display 150, for example, may include a liquid crystal display (LCD), a light emitting diode (LED) display, an organic light emitting diode (OLED) display, a microelectromechanical systems (MEMS) display, or an electronic paper display. The display 150 may display various content (for example, text, image, video, icon, symbol, and so on) to a user. The display 150 may include a touch screen, and for example, may receive a touch, gesture, proximity, or hovering input by using an electronic pen or a user's body part.

According to various embodiments of the present disclosure, the display 150 may output a communication function related user interface. When the detected temperature information satisfies a specified temperature condition, the display 150 may output display data for a function termination schedule time. For example, the display 150 may display information for counting a specific time. The display 150 may output display data for guiding a function termination in correspondence to a function termination schedule time arrival. The display 150 may output display data corresponding to a cool down entry state in correspondence to a specified temperature condition satisfaction. According to various embodiments of the present disclosure, the display 150 may output a specified alarm message in relation to the satisfaction of various specified temperature conditions.

The communication interface 160, for example, may set a communication between the electronic device 100 and an external device (for example, the other electronic device 102 or the server device 104). For example, the communication interface 160 may communicate with an external device (for example, the other electronic device 102 or the server device 104) in connection to the network 162 through wireless communication (or short range wireless communication) or wired communication. The wireless communication may use LTE, LTE-A, CDMA, WCDMA, UMTS, WiBro, or GSM as a cellular communication protocol, for example. The wired communication, for example, may include at least one of universal serial bus (USB), high definition multimedia interface (HDMI), recommended standard 232 (RS-232), and plain old telephone service (POTS). The short range wireless communication may include a communication method based on a Bluetooth communication module, a WiFi direct communication module, and so on.

The communication interface 160 may receive a call connection request from the other electronic device 102. The communication interface 160 may transmit a call connection acceptance to the other electronic device 102 in correspondence to a user control. The communication interface 160 may establish a voice call channel or a video call channel with the other electronic device 102.

According to various embodiments of the present disclosure, in correspondence to a control of at least one of the application processor 30 and the communication processor 20, the communication interface 160 may transmit a function termination schedule time related message to the other electronic device 102 or the server device 104. Additionally, when a communication function is forcibly terminated in correspondence to a function termination schedule time arrival, the communication interface 160 may transmit a specified forced termination guide message (for example, a message for guiding a forced function termination corresponding to temperature condition satisfaction) to the other electronic device 102 or the server device 104 in correspondence to a control of the processor 120. Alternatively, the communication interface 160 may transmit to the other electronic device 102 or the server device 104 a call connection available guide message (for example, information on a call connection available time set experimentally or statistically after forced termination or information for notifying a state that a call connection becomes available corresponding to a temperature condition change after forced termination).

The temperature sensor 180 (for example, a thermistor) may be disposed adjacent to (a position for measuring substantially a temperature of a processor or a corresponding component) at least one (for example, a power control module, the application processor 30, the communication processor 20, a battery, and so on) of hardware of the electronic device 100. The temperature sensor 180 may provide collected temperature information to the processor 120 corresponding to a specific period or a request of a control processor (for example, the communication processor 20 or the application processor 30). According to various embodiments of the present disclosure, the temperature sensor 180 is activated and collects temperature information when a specific application is executed. Alternatively, the temperature sensor 180 may collect temperature information while the electronic device 100 is activated. The temperature sensor 180 may be deactivated when a specific application execution is terminated.

The HRM sensor 190 may collect information on whether a user wears the electronic device 100 or user's heart rate information. The HRM sensor 190, for example, may be activated in synchronization with the activation of the temperature sensor 180. According to an embodiment of the present disclosure, the HRM sensor 190 may be activated in correspondence to a communication function activation. The processor 120 may check whether a user wears the electronic device 100 on the basis of information provided from the HRM sensor 190.

According to various embodiments of the present disclosure, the processor 120 may differently output an alarm message to be outputted corresponding to whether a user wears the electronic device 100. For example, when the electronic device 100 satisfies a specified temperature condition (for example, more than or equal to 38° C.) corresponding to a communication function performance in an unworn state, the processor 120 may perform a message output for inducing the temperature drop of the electronic device 100 (for example, wearing the electronic device 100) in order to maintain a communication function.

According to various embodiments of the present disclosure, the processor 120 may differently change a specified temperature condition corresponding to an unworn state of the electronic device 100. For example, the processor 120 may set a first temperature range (for example, 40° C./104° F., 42° C./107.6° F., or 46° C./114.8° F.) specified in relation to the function termination schedule time, cool down entry, or power-off of the electronic device 100 in a worn state and a second temperature range (for example, 40° C./104° F., 42° C./107.6° F., or 46° C./114.8° F.) specified in relation to the function termination schedule time, cool down entry, or power-off of the electronic device 100 in an unworn state. According to an embodiment of the present disclosure, the processor 120 may set a threshold value for function termination release or cool down release in an unworn state differently from a worn state (for example, more than a worn state). According to various embodiments of the present disclosure, the HRM sensor 190 may be omitted from a configuration of the electronic device 100.

Figure 2:
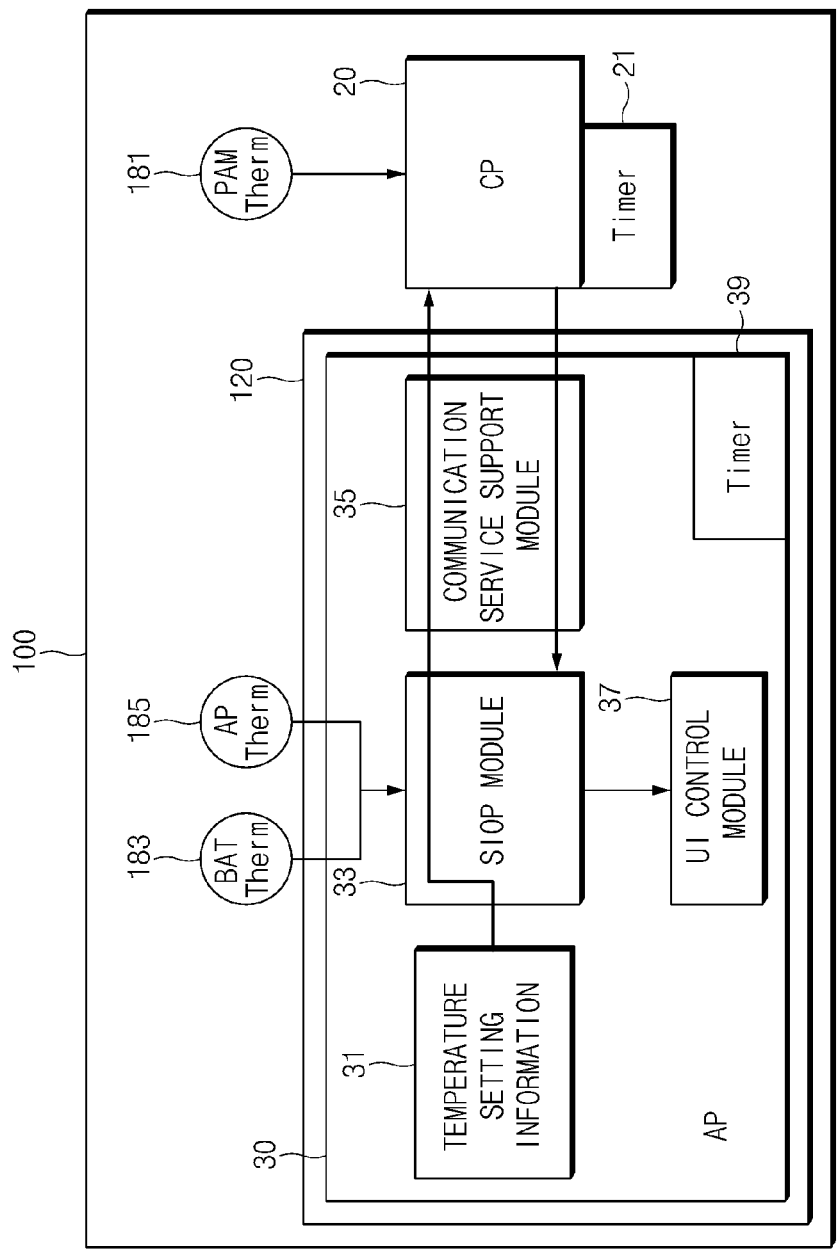
FIG. 2 is a view illustrating a configuration of a processor according to various embodiments of the present disclosure.

FIG. 2 is a view illustrating a configuration of a processor according to various embodiments of the present disclosure. The electronic device 100 may include a processor 120 and at least one temperature sensor (for example, a thermistor). For example, the electronic device 100 may include a battery temperature sensor 183, a temperature sensor 185 for application processor, and a temperature sensor 181 for communication module.

The battery temperature sensor 183 may detect a battery temperature and may deliver the detected temperature information to the SIOP module 33. The battery temperature sensor 185 may detect a battery temperature and may deliver the detected temperature information to a Samsung intelligent overheating protecting (SIOP) module 33. The temperature sensor 181 for communication module may perform a temperature detection corresponding to a control of the communication processor 20 or in a specific period and may deliver the detected temperature information to the communication processor 20. The communication processor 20 may deliver the detected temperature information to the SIOP 33.

The processor 120 may include an application processor 30 and a communication processor 20. The application processor 30 may include temperature setting information 31, a SIOP module 33, a user interface (UI) control module 37, a communication service support module 35, and a timer 39. The communication service support module 35 can include, among other things, a telephony service support module.

The temperature setting information 31 may include function control information corresponding to temperature information of the electronic device 100. For example, the temperature setting information 31 may include constrained temperature condition information, restricted temperature condition information, and limited temperature condition information.

When information on a first temperature range (for example, 38° C. to 42° C./107.6° F.) and detected temperature information are within the first temperature range, the constrained temperature condition information may include a driving setting of the timer 39 and information output setting corresponding to the driving of the timer 39. Additionally, the constrained temperature condition information may include a setting for the termination of at least one function among functions in execution when the timer 39 expires. For example, the constrained temperature condition information may include at least one of a setting for terminating a function relating to hardware having the highest current consumption, a setting for terminating a function corresponding to a priority specified for each function, a setting for terminating the oldest function among functions in execution, and a setting for terminating the recently executed function, when the timer 39 expires. According to an embodiment of the present disclosure, when the constrained temperature condition is satisfied during a management process of the recently executed function (for example, a communication function), the constrained temperature condition information may include a setting for terminating the recently executed function when the timer 39 expires.

The restricted temperature condition information may include information on a second temperature range (for example, 42° C./107.6° F. to 46° C./114.8° F.) and a setting for performing cool down processing when the detected temperature information is within the second temperature range. The restricted temperature condition information may include a setting for cool down release after cool down processing. A setting for cool down release may include information on a function (for example, a data communication function or a voice communication function) restricted by cool down and an unrestricted function (for example, an emergency call function).

The limited temperature condition information may include information on a third temperature range (for example, more than 46° C./114.8° F.) and a setting for performing power off processing when the detected temperature information is within the third temperature range.

The above temperature setting information 31 may be adjusted by a user setting. In relation to this, the application processor 30 may provide a screen interface relating to the adjustment of the temperature setting information 31. A user may adjust the first temperature range to the third temperature range on the basis of the temperature setting information adjustment screen. The electronic device 100 may allow the first temperature range to third temperature range adjustment within an experimental or statistical range in which hardware damage does not occur. For example, in correspondence to whether the electronic device 100 is allowed, a user may adjust the first temperature range to a range of less than 38° C., the second temperature range to a range of 38° C. to 42° C./107.6° F., and the third temperature range to a range of more than 46° C./114.8° F. Alternatively, in correspondence to whether the electronic device 100 is allowed, a user may adjust the first temperature range to 40° C./104° F., the second temperature range to 42° C./107.6° F., and the third temperature range to 46° C./114.8° F. The above temperature range adjustment is just one example and may vary depending on temperature resistance characteristics of the electronic device 100 and a user's setting change.

The SIOP module 33 may perform a temperature detection in correspondence to a specific period or an event occurrence (for example, a communication function execution) and may restrict at least one function in execution on the basis of the detected temperature information. According to an embodiment of the present disclosure, the SIOP module 33 may restrict a communication function on the basis of at least one of temperature information provided from the battery temperature sensor 183, the temperature sensor 185 for application processor, and the communication processor 20. For example, the SIOP module 33 may restrict a communication function on the basis of an average temperature value, the maximum temperature value, or the minimum temperature value of battery temperature information, temperature information for an application processor, and temperature information for a power control module. According to an embodiment of the present disclosure, after assigning a weight to battery temperature information, temperature information for an application processor, and temperature information for a power control module, the SIOP module 33 may restrict a communication function on the basis of temperature information calculation corresponding to a weight. For example, the SIOP module 33 may assign a relatively high weight to temperature information for application processor during a process for performing a data communication function in comparison to another temperature information. The SIOP module 33 may assign a relatively high weight to temperature information for power control module during a process for performing a call function in comparison to another temperature information.

The SIOP module 33 may control the driving of the timer 39 in relation to communication function restriction. According to an embodiment of the present disclosure, the SIOP module 33 may compare temperature information that the temperature sensor 181 for communication module delivers to the communication processor 20 with the temperature setting information 31. The SIOP module 33 may drive the timer 39 in which detected temperature information satisfies a constrained temperature condition. Additionally, the SIOP module 33 may output notification information relating to the timer 39 to the UI control module 37. When the driving of the timer 39 is terminated, the SIOP module 33 may request a communication function termination from the communication processor 20.

The SIOP module 33 may control cool down (for example, app termination) or power off corresponding to the detected temperature information. For example, the SIOP module 33 may control cool down processing when detected temperature information satisfies a restricted temperature condition. In relation to the cool down processing, the SIOP module 33 may request related function processing from the UI control module 37. Additionally, the SIOP module 33 may process power off when detected temperature information satisfies a limited temperature condition. In relation to the power off, the SIOP module 33 may request a guide information output from the UI control module 37.

According to various embodiments of the present disclosure, the SIOP module 33 may terminate a call function within a specified first temperature range (for example, a specified temperature range for function termination). After the call function termination, the SIOP module 33 may perform a call function corresponding to a re-call attempt and perform temperature detection. When detected temperature information approaches a specified second temperature range (for example, a specified temperature range for cool down execution) (for example, when a specified temperature is 42° C./107.6° F.), a notification message for notifying cool down execution or communication function restriction may be outputted. A notification message, for example, may be outputted as a specified beep sound, vibration, text, or image. The above-mentioned function may be applied to the first temperature range. For example, in a case that the first temperature range is specified to 40° C./104° F., if temperature information corresponding to 38° C. or 39° C. is detected, the SIOP module 33 may output a notification message notifying that a communication function is able to be restricted.

The UI control module 37 may output display data in correspondence to a request from the SIOP module 33. For example, the UI control module 37 may output audio data corresponding to a timer count through the input/output interface 170 or may output display data corresponding to a timer count to the display 150 in relation to the driving of the timer 39. The UI control module 37 may process at least one alarm message output corresponding to a temperature condition (at least one of a state that the constrained temperature condition is satisfied, a state that the restricted temperature condition is satisfied, and a state that the limited temperature condition is satisfied) corresponding to the detected temperature information through at least one of the input/output interface 170 and the display 150.

According to various embodiments of the present disclosure, the UI control module 37 may output a communication function control related virtual button to a screen where display data corresponding to a timer count is outputted. The UI control module 37 may output a function termination screen in correspondence to the completion of the timer 39.

After the function termination, the UI control module 37 may output a communication function usage related virtual button.

According to various embodiments of the present disclosure, the UI control module 37 may process input restriction according to a cool down state. For example, the UI control module 37 may perform a touch function related hardware control (for example, touch panel deactivation and touch activation during emergency call execution). The UI control module 37 may deactivate a communication function execution related physical key button or virtual button.

The communication service support module 35 may communicate with the communication processor 20 in relation to a communication function support of the electronic device 100. For example, the communication service support module 35 may request a communication channel establishment with the other electronic device 102 or the server device 104 from the communication processor 20 in relation to a communication function execution request. The communication service support module 35 may receive a call sound or data that the communication processor 20 receives and may provide this to a related application (for example, a communication function application).

According to various embodiments of the present disclosure, the communication service support module 35 may receive temperature information for a power control module from the communication processor 20 corresponding to a request of the SIOP module 33 or a specific period and may deliver the temperature information to the SIOP module 33. The communication service support module 35 may deliver a communication function termination request to the communication processor 20 corresponding to a request of the SIOP module 33.

The timer 39 may be driven corresponding to a control of the SIOP module 33. A driving time of the timer 39 may be adjusted. According to various embodiments of the present disclosure, the timer 39 may support various schedule time settings. For example, the timer 39 may support a count corresponding to a function termination schedule time (for example, a time taken for terminating a communication function) depending on the constrained temperature condition satisfaction. Additionally, the timer 39 may support a count corresponding to a basic communication performance time set to maintain a communication function during a specific time while a communication function is executed.

The communication processor 20 may support a communication function corresponding to a control of the application processor 30. For example, when receiving a request for communication channel establishment from the communication service support module 35, the communication processor 20 may control the communication interface 160 to establish a communication channel with the other electronic device 102 or the server device 104. The communication processor 20 may deliver communication data received through the communication interface 160 to the communication service support module 35 of the application processor 30.

The communication processor 20 may process a communication channel release in correspondence to a communication function termination request of the SIOP module 33. In relation to this, the communication processor 20 may transmit a function termination schedule time to the other electronic device 102 or the server device 104. The communication processor 20 may transmit a function termination schedule time arrival or a function termination corresponding to cool down or power-off to the other electronic device 102 or the server device 104.

The communication processor 20 may include the SIOP module 33, a UI control module 37, and a timer 21. In this case, the communication processor 20 may perform a function restriction corresponding to the temperature condition satisfaction separately from the application processor 30. Alternatively, the communication processor 20 may process a function restriction corresponding to the temperature condition satisfaction when the application processor 30 is in a sleep state. According to an embodiment of the present disclosure, the communication processor 20 compares temperature information for a power control module and the temperature setting information 31 and may drive the timer 21 corresponding to a comparison result. Similarly to the timer 39, the timer 21 may be used for counting a function termination schedule time or a basic communication performance time. When the communication processor 20 includes the timer 21, the timer 39 of the application processor 30 may be omitted.

An electronic device may include a communication interface for supporting a communication function and a process for driving a timer for warning of a communication function termination when detected temperature information satisfies a specified temperature condition according to the communication function execution.

The processor may be set to maintain the communication function execution during a basic communication performance time specified before an operation for performing the temperature detection.

The processor may be set to maintain the communication function execution during a specified basic communication performance time when the obtained temperature information satisfies a specified temperature condition after the temperature detection performance.

The processor may be set to perform a temperature detection again after the basic communication performance time elapses, drives the timer when the obtained temperature information satisfies a specified temperature condition, and output count information corresponding to the timer driving.

The process may be set to output at least one of display data and audio data corresponding to the count information.

The processor may be set to output at least one of a virtual key button set to maintain a communication function during the timer driving time, a virtual key button set to terminate the communication function, and a virtual key button for delaying a communication function termination corresponding to the timer driving for a specific time.

When the timer driving expires, the processor may be set not to reuse the communication function for a specific time.

When the specific time elapses, the processor may be set to output information relating to the communication function reuse availability.

The processor may be set to power off by cutting power supply when the timer driving expires, or power off by cutting power supply when a re-performed temperature detection result satisfies a specified limited temperature condition after the timer driving expires.

The processor may be set to transmit to the other electronic device at least one of a communication function termination schedule time or the communication function termination corresponding to the timer driving.

When temperature information detected during the timer driving satisfies a specified limited temperature condition, the processor may be set to power off by cutting power supply.

An electronic device may include a memory for storing at least one instruction and at least one processor for executing the instruction in connection to the memory. The instruction executed by the at least one processor may be set to detect temperature information of the electronic device during the communication function execution, drive a timer for warning a communication function termination if the detected temperature information satisfies a specified temperature condition, and output count information corresponding to the timer driving. Alternatively, an electronic device may include a memory for storing at least one instruction and at least one processor for executing the instruction in connection to the memory. The electronic device may be set to check whether temperature information of the electronic device satisfies a specified temperature condition when a communication function is executed and maintain a communication function execution during a basic communication performance time when the temperature information satisfies the specified temperature condition.

The instruction may be set to detect temperature information of the electronic device again after the basic communication performance time elapses, drive a timer for warning a communication function termination when the redetected temperature information satisfies a specified temperature condition, and output count information corresponding to the timer driving.

Alternatively, an electronic device may include a memory for storing at least one instruction and at least one processor for executing the instruction in connection to the memory, and may be set to maintain a communication function execution during a basic communication performance time of an automatically specific size when a communication function is executed, detect temperature information of the electronic device after the basic communication performance time elapses, drive a timer for warning a communication function termination if the detected temperature information satisfies a specified temperature condition, and output count information corresponding to the timer driving.

Figure 3:
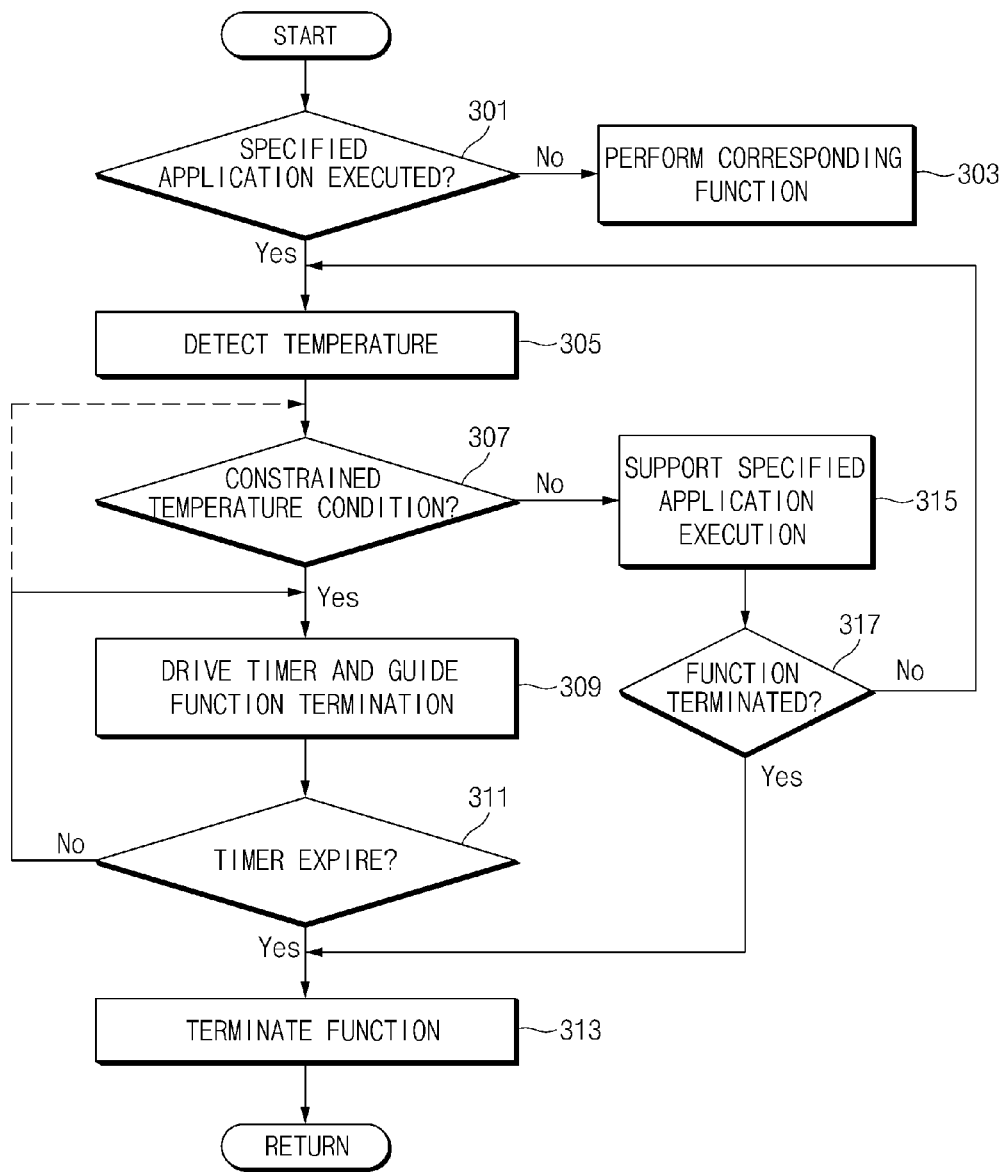
FIG. 3 is a flowchart illustrating a function controlling method according to various embodiments of the present disclosure.

FIG. 3 is a flowchart illustrating a function controlling method according to various embodiments of the present disclosure. FIG. 3 describes the circumstance of when the constrained temperature condition occurs. When the constrained temperature condition, a timer is set for termination of a function. When an input event occurs, the electronic device 100 may check whether the input event relates to a specific application execution in operation 301. If the occurred input event is not an input event (for example, an event relating to a call connection request reception or a call connection attempt, a web access request event, and so on) relating to a communication function (for example, a voice call function, an image call function, a data communication function, and so on), the electronic device 100 may process a function performance corresponding to the input event in operation 303. For example, the electronic device 100 may play content or detect a biometric signal to support detected information processing in correspondence to the type of an input event.

When an input event relating to a specific application execution, the electronic device 100 may support an application execution corresponding to an input event type. For example, the electronic device 100 may provide a voice call function, an image call function, a data communication function, a content streaming reception and output function, a broadcast reception function, and a voice search function corresponding to an input event type. When a specific application is executed, the electronic device 100 may perform a temperature detection in operation 305. For example, when a communication related application is executed, the electronic device 100 may collect temperature information from the temperature sensor 181 for communication module. The electronic device 100 may compare the detected temperature information and the temperature setting information 31.

In operation 307, the electronic device 100 may check whether it is a constrained temperature condition. For example, the electronic device 100 may check whether the detected temperature information is within a specified first temperature range. When the detected temperature information is more than a constrained temperature, the electronic device 100 may perform a timer driving and a function termination guide in operation 309. A timer may count a specific time. The electronic device 100 may output information counted corresponding to a timer driving to at least one of the input/output interface 170 and the display 150. When the timer driving expires, the electronic device 100 may output a function termination guide (for example, at least one of audio data and display data) for warning that a function in execution is to be terminated.

In operation 311, the electronic device 100 may check whether a timer expires. Before a timer expires, the electronic device 100 may branch into operation 309 and perform subsequent operations again. According to various embodiments of the present disclosure, before a timer expires, the electronic device 100 may branch into operation 307 and perform subsequent operations again. For example, the electronic device 100 may support a communication function in execution.

When a timer expires, the electronic device 100 may process a function termination in operation 313. For example, the electronic device 100 may process a communication channel release in relation to a communication function termination. Additionally, the electronic device 100 may terminate an application executed in relation to a communication function.

When the detected temperature information does not satisfy a constrained temperature condition, the electronic device 100 may support a specific application execution in operation 315. For example, when the detected temperature information is within a first temperature range, the electronic device 100 may perform processing to maintain a specific application execution.

In operation 317, the electronic device 100 may check whether there is an event occurrence relating to a function termination. When a function termination related event occurs, the electronic device 100 may perform function termination processing in operation 313. If there is no function termination related event, the electronic device 100 may branch into operation 305 and perform subsequent operations again.

Figure 4:
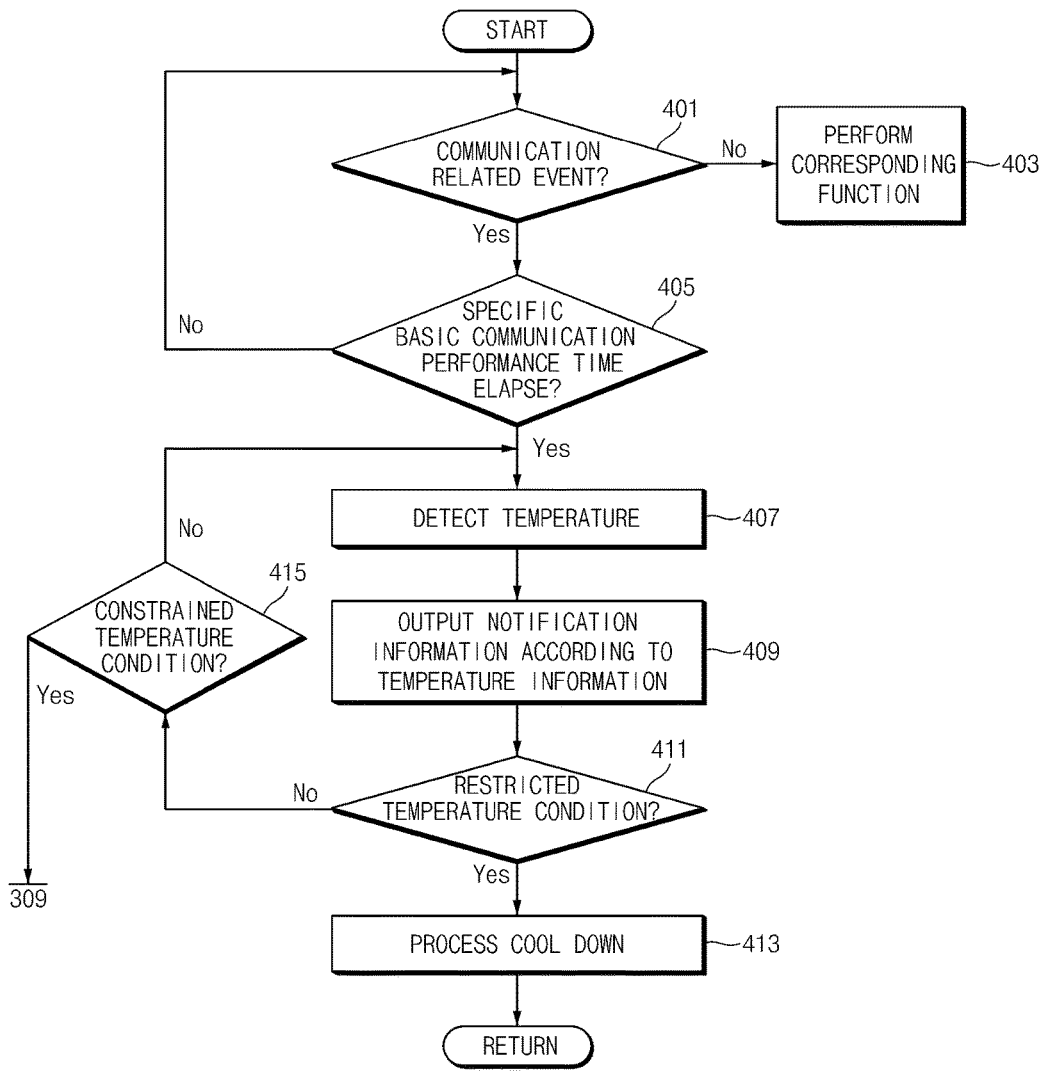
FIG. 4 is a flowchart illustrating a communication function controlling method according to various embodiments of the present disclosure.

FIG. 4 is a flowchart illustrating a communication function controlling method according to various embodiments of the present disclosure, wherein the electronic device 100 allows a period of time to elapse prior to checking the temperature. If after checking the temperature, the restricted temperature condition occurs, the electronic device 100 processes cool down measures. If after checking the temperature, the constrained temperature condition occurs, the electronic device 100 sets a timer for terminating the communication function.

When an event occurs, the electronic device 100 may check whether a communication function related event occurs in operation 401. If no communication function related event occurs, the electronic device 100 may process a function performance corresponding to the occurred event in operation 403. For example, the electronic device 100 may process the playback of stored music content or support a watch function corresponding to an event type. Alternatively, the electronic device 100 may support a message check function.

If a communication function related event occurs, the electronic device 100 may process a communication function performance. For example, the electronic device 100 may execute a communication function related application and may establish a voice call channel or a video call channel with the other electronic device 102. During this operation, the electronic device 100 may count a specified basic communication performance time. The electronic device 100 may output information counted in relation to the basic communication performance time.

In operation 405, the electronic device 100 may check whether the specific basic communication performance time elapses. If a communication function termination related event occurs within the basic communication performance time, the electronic device 100 may process a communication function termination. If the basic communication performance time does not elapse, the electronic device 100 may support a communication function performance in operation 401.

If the basic communication performance time elapses, the electronic device 100 may perform a temperature detection in operation 407. The electronic device 100 may compare the detected temperature information and the temperature setting information 31. In operation 409, the electronic device 100 may process a notification information output corresponding to temperature information. For example, when the detected temperature information is within a first temperature range, the electronic device 100 may warn a function termination schedule time corresponding to the satisfaction of a constrained temperature condition. When a corresponding time elapses (for example, when the function termination schedule time elapses), the electronic device 100 may output notification information for guiding that a function is to be terminated. Alternatively, when the detected temperature information is within a second temperature range and thus satisfies a specified restricted temperature condition, the electronic device 100 may warn the execution of a cool down function (for example, a function for processing a specified function not to be used during a specific time) and may output notification information for guiding that a function usage according thereto is unavailable. Alternatively, when the detected temperature information is within a third temperature range and thus satisfies a limited temperature condition, the electronic device 100 may warn power off. During this operation, the electronic device 100 may perform a control to output count information of a specific timer. For example, the electronic device 100 may output specific timer count information for a warning time point at which a cool down function is to be executed. Alternatively, the electronic device 100 may output specific timer count information for a warning time point at which power off is executed. According to various embodiments of the present disclosure, a notification information output corresponding to temperature information in operation 409 may be omitted.

In operation 411, the electronic device 100 may check whether the detected temperature information satisfies a restricted temperature condition corresponding to a specified second temperature range. For example, the electronic device 100 may check whether the detected temperature information is more than 42° C./107.6° F. When the restricted temperature condition is satisfied (for example, the detected temperature information is more than 42° C./107.6° F.), the electronic device 100 may perform cool down processing in operation 413. In relation to the cool down processing, the electronic device 100 may terminate a communication function in execution and may perform processing not to reuse the communication function for a specific time. According to various embodiments of the present disclosure, the electronic device 100 may perform cool down processing at the restricted temperature condition satisfaction time point or may drive a timer to perform cool down processing after a timer driving completion.

When the temperature information does not satisfy the restricted temperature condition (for example, in the case of a second temperature range), the electronic device 100 may check whether the constrained temperature condition is satisfied in operation 415. When the detected temperature information does not satisfy the constrained temperature condition (for example, the detected temperature information is within a specified first temperature range), the electronic device 100 may branch into operation 407 and perform subsequent operations. When the detected temperature information is more than the first temperature range, the electronic device 100 may branch into operation 309 described with reference to FIG. 3 and process subsequent processes.

Figure 5:
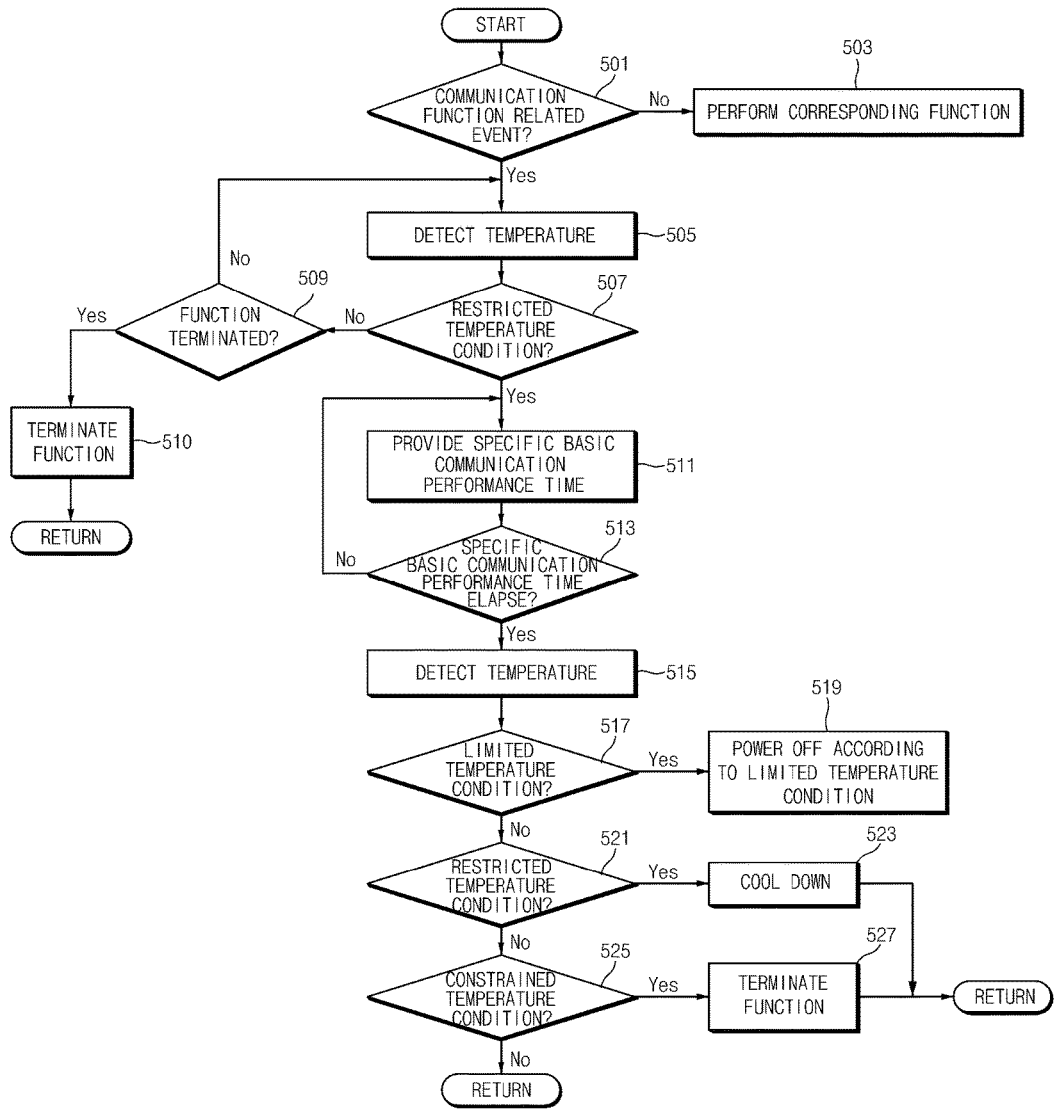
FIG. 5 is a flowchart illustrating a temperature specific communication function controlling method according to various embodiments of the present disclosure.

FIG. 5 is a flowchart illustrating a temperature specific communication function controlling method according to various embodiments of the present disclosure. The electronic device 100 checks the temperature for a restricted temperature condition. If the restricted temperature condition occurs, after a specific basic communication performance time has elapsed, the temperature is checked again. Based on the rechecked temperature, a determination is made whether there is a limited temperature condition, a restricted temperature condition, or a constrained temperature condition. If there is a limited temperature condition, the electronic device powers off at least a portion of the electronic device. If there is a restricted temperature condition, the electronic device 100 takes cool down measures. If there is a constrained temperature condition, the electronic device 100 terminates the function. The electronic device 100 may check whether the occurred event type is a communication function related event in operation 501. If the event is not a communication function related event, the electronic device 100 may process a function performance corresponding to the event type in operation 503. If the communication function related event occurs, the electronic device 100 may perform a temperature detection in operation 505.

In operation 507, the electronic device 100 may check whether the detected temperature information satisfies a constrained temperature condition (for example, it is within a first temperature range). When the constrained temperature condition is not satisfied (for example, the detected temperature information is less than 40° C./104° F.), the electronic device 100 may check whether a function termination related event occurs in operation 509. If there is no function termination related event, the electronic device 100 may branch into operation 505 and perform subsequent operations again while supporting a communication function. When a function termination related event occurs, the electronic device 100 may perform function termination processing in operation 510.

When the detected temperature information satisfies the constrained temperature condition (for example, more than 40° C./104° F.), the electronic device 100 may provide a specific basic communication performance time in operation 511. The basic communication performance time, for example, may be set by several sec to several min and may be adjusted corresponding to a user setting.

In operation 513, the electronic device 100 may check whether the specific basic communication performance time elapses. If the basic communication performance time does not elapse, the electronic device 100 may branch into operation 511 and support a communication function during the basic communication performance time. If a function termination related event occurs during the basic communication performance time, the electronic device 100 may process a communication function termination.

If the basic communication performance time elapses, the electronic device 100 may perform a temperature detection again in operation 515. In operation 517, the electronic device 100 may check whether the detected temperature information satisfies a limited temperature condition. The limited temperature condition, for example, may be a case that the detected temperature information is within a third temperature range (for example, more than 46° C./114.8° F.). If it is the limited temperature condition, the electronic device 100 may process power off corresponding to the limited temperature condition in operation 519. If the limited temperature condition is satisfied during this operation, the electronic device 100 may process power off. Alternatively, if the limited temperature condition is satisfied, the electronic device 100 may drive a timer and process power off when the timer expires.

When the limited temperature condition is not satisfied, for example, the detected temperature information is less than 46° C./114.8° F., the electronic device 100 may check whether the restricted temperature condition is satisfied in operation 521. When the detected temperature information satisfies the restricted temperature condition (for example, less than 46° C./114.8° F. and more than 42° C./107.6° F.), the electronic device 100 may perform cool down processing in operation 523. During this operation, while detecting a temperature change, the electronic device 100 may process cool down at the time point that the restricted temperature condition is satisfied. Alternatively, if the restricted temperature condition is satisfied, the electronic device 100 may drive a timer and process cool down when the timer expires. After the cool down processing, the electronic device 100 may maintain a cool down state for a specific time. When a cool down maintenance time expires, the electronic device 100 may return to a state before communication function execution.

When the restricted temperature condition is not satisfied (for example, the detected temperature information is less than 42° C./107.6° F.), the electronic device 100 may check whether the constrained temperature condition is satisfied in operation 525. When the detected temperature information satisfies a constrained temperature condition, the electronic device 100 may process function termination in operation 527. During this operation, the electronic device 100 may process function termination at the time point that the constrained temperature condition is satisfied. Alternatively, if the constrained temperature condition is satisfied, the electronic device 100 may drive a timer and process function termination when the timer expires. After the function termination processing, the electronic device 100 may return to a specified state. For example, the electronic device 100 may return to a state before communication function execution.

When the constrained temperature condition is not satisfied (for example, the detected temperature information is less than 40° C./104° F.), the electronic device 100 may return to a communication function support state. For example, the electronic device 100 may branch into operation 501 or branch into operation 515.

A driving time of a timer driven corresponding to a limited temperature condition, a driving time of a timer driven corresponding to a restricted temperature condition, and a driving time of a timer driven corresponding to a constrained temperature condition may be different from each other. For example, a limited temperature condition timer driving time may be set relatively shorter than another driving time. Alternatively, a restricted temperature condition timer driving time may be set shorter than a constrained temperature condition timer driving time.

A function controlling method may include performing a temperature detection corresponding to a communication function execution, driving a timer for warning of communication function termination when temperature information detected corresponding to the temperature detection satisfies a specified temperature condition, and outputting count information corresponding to the timer driving.

The method may further include maintaining the communication function execution during a basic communication performance time specified before the performing of the temperature detection.

The method may further include maintain communication function execution during a specified basic communication performance time when the obtained temperature information satisfies a specified temperature condition after the performing of the temperature detection.

The driving of the timer may include performing a temperature detection again after the basic communication performance time elapses and driving the timer when the obtained temperature information satisfies a specified temperature condition.

The outputting of the count information may include at least one of display data corresponding to the count information and outputting audio data corresponding to the count information.

The outputting of the count information may further include outputting at least one of a virtual key button set to maintain a communication function during the timer driving time, a virtual key button set to terminate the communication function, and a virtual key button for delaying a communication function termination corresponding to the timer driving for a specific time.

The method may further include, when the timer driving expires, processing not to reuse the communication function for a specific time.

The method may further include, when the specific time elapses, outputting information relating to the communication function reuse availability.

The method may further include performing power off by cutting power supply when the timer driving expires.

The method may further include transmitting at least one of a communication function termination schedule screen and a communication function termination corresponding to the timer driving.

Figure 6:
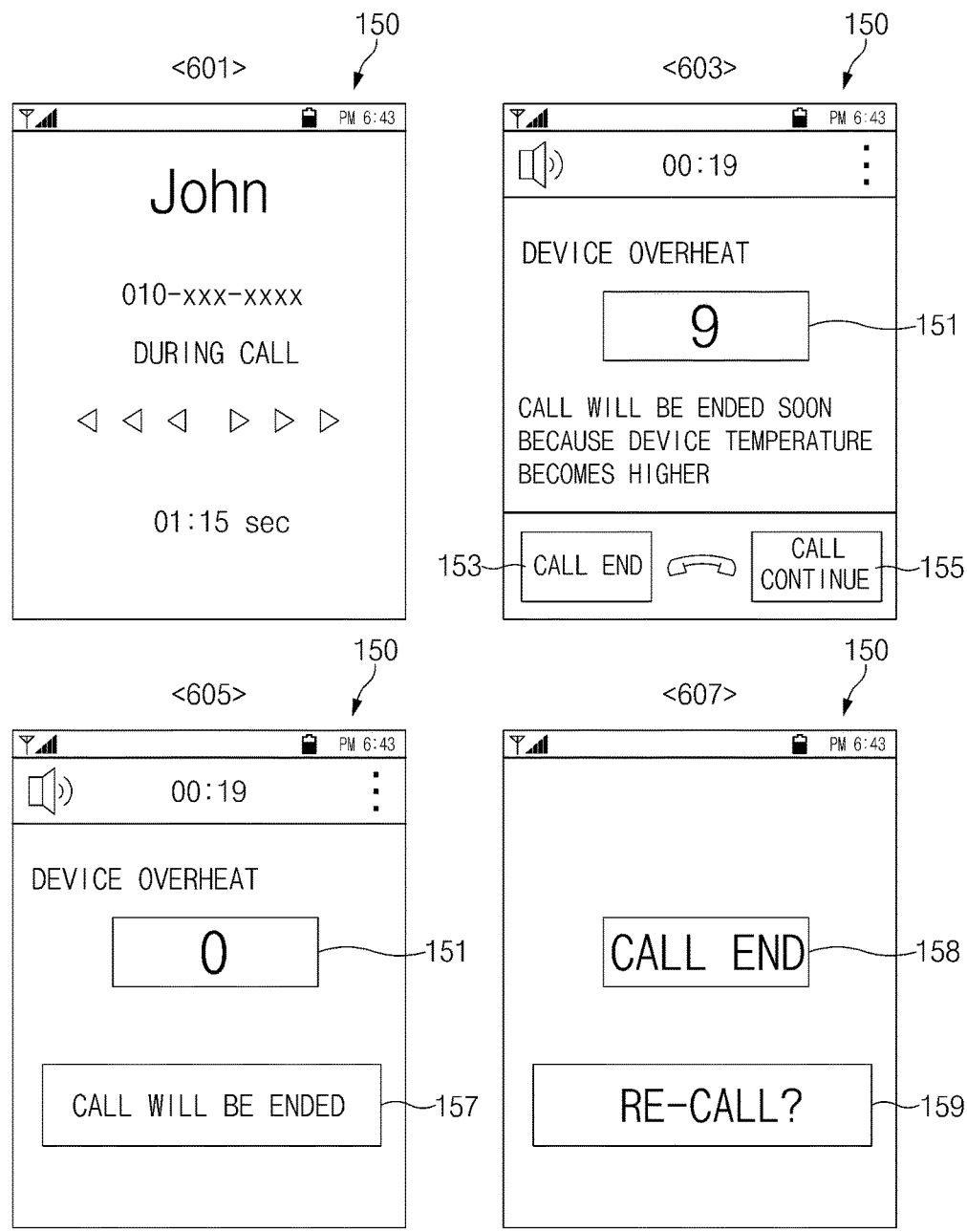
FIG. 6 is a view illustrating a function control related screen interface according to various embodiments of the present disclosure.

FIG. 6 is a view illustrating a function control related screen interface according to various embodiments of the present disclosure. FIG. 6 will be described with respect to the flow diagrams of FIGS. 3 and 4.

As shown in a state 601, the electronic device 100 may output a screen corresponding to a call function execution. For example, when accepting a call connection request from the other electronic device 102, the electronic device 100 may output a screen corresponding to a call function execution. Alternatively, the electronic device 100 may transmit a call connection request to the other electronic device 102 in correspondence to a phone number input or an input event for selecting connection information of the other electronic device 102 included in a phonebook. The electronic device 100 may output a screen corresponding to a call function execution in correspondence to the acceptance of the other electronic device 102 for a call connection request.

The electronic device 100 may perform a temperature detection (such as operation 305) during a call function execution. Alternatively, after a call function execution, as a basic call performance time (for example, several min) (such as completion of the elapsed time during operation 405), the electronic device 100 may perform temperature detection (such as operation 407). When the detected temperature information satisfies a constrained temperature condition (such as the condition of operation 307), as shown in a state 603, a screen relating to a function termination schedule time may be outputted to the display 150. For example, a function termination schedule time may output guide information (for example, a guide for device temperature rise) corresponding to the satisfaction of a constrained temperature condition. Additionally, the function termination schedule screen may include timer information 151, a call end button 153, and a call hold button 155. The timer information 151 may be information counted corresponding to timer driving. The call end button 153 may be a virtual button set to terminate a call function in execution. The call hold button 155 may be a virtual button set to continue a call during a time counted by a timer (such as operation 309).

According to various embodiments of the present disclosure, as shown in a state 605, the electronic device 100 may output information corresponding to a timer elapse (such as operation 409). A screen corresponding to a timer elapse, for example, may include timer information 151 and guide information 157 for guiding a function to be executed corresponding to timer expiration. The timer information 151 may be changed corresponding to a timer count. For example, when the counter of the timer information 151 indicates 9 in a state 603, the timer information 151 may indicate that the counter is terminated in a state 605. An output of information corresponding to a timer elapse may be outputted. Alternatively, an information output corresponding to a timer elapse may be outputted intermittently (for example, a several sec unit). Additionally/alternatively, the electronic device 100 may replace information corresponding to a timer elapse with audio data processing.

When a timer expires (such as the condition of operation 311), the electronic device 100 may perform function termination processing (such as operation 313) as shown in a state 607. The function termination screen, for example, may include information 158 for guiding call function termination and a re-call button 159. The re-call button 159 may be a virtual button set to automatically perform a call connection with the other electronic device 102 that is connected right before. The re-call button 159 may be activated or deactivated in correspondence to the detected temperature information. According to various embodiments of the present disclosure, the electronic device 100 performs a temperature detection after the timer driving is completed and may finally determine a function termination corresponding to the detected temperature information. For example, when the detected temperature information still satisfies the constrained temperature condition (such as the condition of operation 415), the electronic device 100 may terminate a call function (operation 313). Alternatively, when the detected temperature information satisfies a restricted temperature condition (such as the condition of operation 411), the electronic device 100 may perform cool down processing (operation 413) for a call function with a call function termination. During this operation, the electronic device 100 may deactivate the re-call button 159. The electronic device 100 may perform a control to activate the re-call button 159 after a specific time (for example, a time set for cool down release) elapses.

Figure 7:
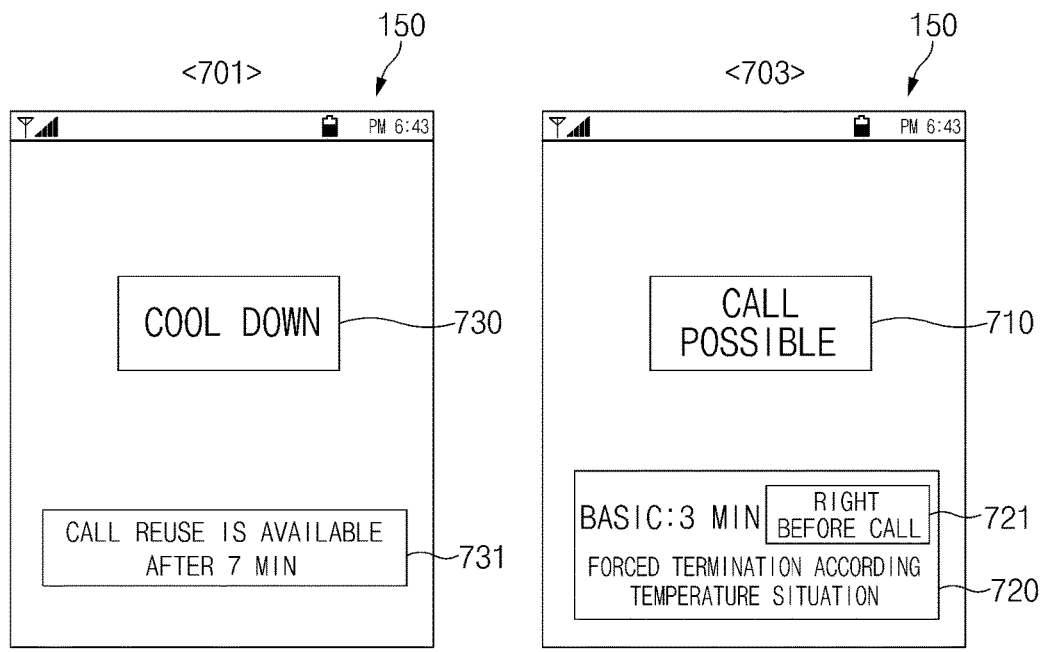
FIG. 7 is a view illustrating a communication function related screen interface according to various embodiments of the present disclosure.
Figure 8:
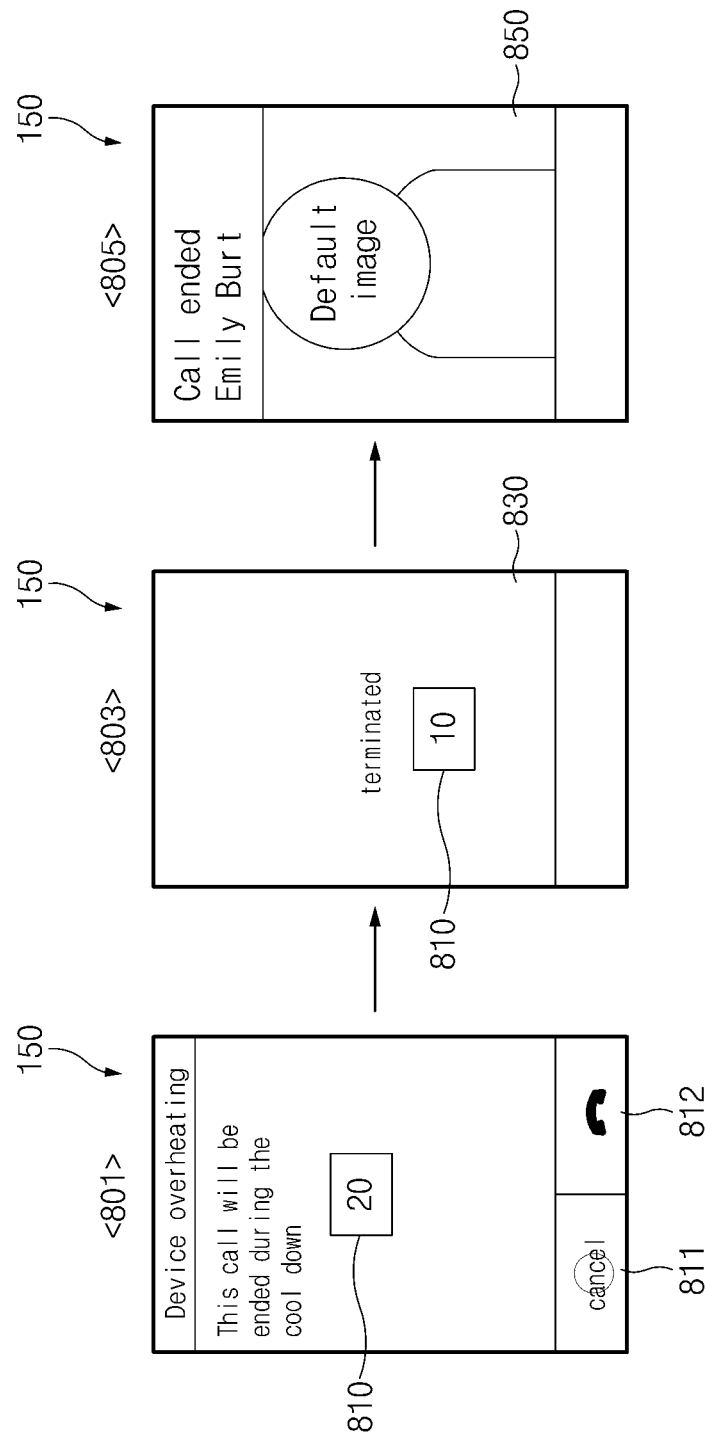
FIG. 8 is a view illustrating a function control screen interface on the basis of a constrained temperature condition according to various embodiments of the present disclosure.

Screen interfaces will now be described with references to FIGS. 7-9 for various operations described above. FIG. 7 describes a screen interface that may be used during cool down operation 413 or 523 when the restricted temperature conditions occurs such as in operations 411 or 521. FIG. 8 describes screen interfaces that may be used during the terminate function operation 313 or 527 during a constrained temperature condition 311 or 525.

FIG. 7 is a view illustrating a communication function related screen interface according to various embodiments of the present disclosure. The electronic device 100 performing a temperature detection during a communication function performance may perform cool down processing when the detected temperature information satisfies a restricted temperature condition. Correspondingly, the electronic device 100, as shown in a state 701, may output guide information 730 corresponding to cool down processing. The guide information 730 may be continuously or intermittently outputted during a cool down maintenance period. Alternatively, the guide information 730 may be outputted when a specified key button input or an event for requesting the activation of the display 150 occurs. The guide information 730 may be changed to audio data processing additionally or alternatively.

Additionally, the electronic device 100 may output call availability schedule information 731 relating to a cool down release. The call availability schedule information 731 may be set based on experimentally or statistically obtained data (for example, experimental data from a restricted temperature state to a time point at which the electronic device 100 is changed to a state of less than a specified temperature, for example, 36° C./96.8° F.). Alternatively, the call availability schedule information 731 may be adjusted corresponding to a user setting. According to various embodiments of the present disclosure, the call availability schedule information 731 may vary depending on hardware characteristics of the electronic device 100 or characteristics of a region where the electronic device 100 is sold.

According to various embodiments of the present disclosure, the call availability schedule information 731 may be differently changed and outputted corresponding to a real time temperature detection of the electronic device 100. For example, the electronic device 100 may perform a temperature detection in real time or in a specific period in a call function termination and activation suppression state (for example, a state in which a function access is blocked temporarily not to allow a call function) corresponding to cool down processing. When the detected temperature information satisfies a specified temperature, for example, a constrained temperature condition (for example, 40° C./104° F.), the electronic device 100 may adjust the call availability schedule information 731 (for example, adjust 7 min to 3 min) and output it. According to various embodiments of the present disclosure, when the detected temperature information is changed to a specified temperature, for example, a less than 38° C./100.4° F., the electronic device 100 may change the call availability schedule information 731 into the call availability guide information 720, as shown in a state 703. According to various embodiments of the present disclosure, when the detected temperature information is out of a restricted temperature condition, for example, a less then 42° C./107.6° F., the electronic device 100 may change the call availability schedule information 731 into the call availability guide information 720, as shown in a state 703.

In correspondence to cool down release, the electronic device 100 may remove the guide information 730 corresponding to cool down processing and may output the call availability notification information 710 as shown in a state 703. The call availability notification information 710 may include rule information 720 applied during a call. The call availability notification information 710 may output a right before call virtual button 721 for re-performing a call performed right before cool down processing. When the right before call virtual button 721 is selected, the electronic device 100 may automatically re-perform a call function performed right before cool down processing. For example, the electronic device 100 may automatically attempt a call connection with another electronic device.

FIG. 8 is a view illustrating a function control screen interface on the basis of a constrained temperature condition according to various embodiments of the present disclosure. When a specified constrained temperature condition is satisfied due to a temperature rise of a device during a process for performing a call function, the electronic device 100 may output a timer screen for warning a function termination to the display 150 as shown in a state 801. The timer screen, for example, may include timer count information 810, a call termination virtual button 810, and a call end delay virtual button 812. When the call termination virtual button 811 is selected, the electronic device 100 may terminate a call function. If the call termination virtual button 811 is not selected additionally, the timer count information 810 may be changed as a timer counter increases. When the call end delay virtual button 812 is selected, the electronic device 100 may delay a call termination function corresponding to timer expiration for a specific time. For example, the electronic device 100 may stop timer driving and provide a basic call performance time. During this operation, the electronic device 100 may output display data relating to the basic call performance time offer to the display 150. The electronic device 100 may perform a temperature detection again after the basic call performance time elapses and may perform timer driving and function termination corresponding to the detected temperature information.

When the timer count information is changed to less than a specified value (for example, less than 10 sec), the electronic device may output a function termination warning screen 830 as shown in a state 803. The function termination warning screen 830 may include a function termination schedule time 811. The function termination schedule time 811 may be changed corresponding to a timer count.

When the function termination schedule time 811 elapses, as shown in a state 805, the electronic device 100 may output a screen 850 corresponding to a function termination to the display 150. For example, the function termination screen 850 may include information (for example, caller information, caller image information, and so on) relating to a call performed before a call function termination. According to various embodiments of the present disclosure, the electronic device 100 may store call log information on a terminated function in correspondence to the elapse of the function termination schedule time 811.

Figure 9:
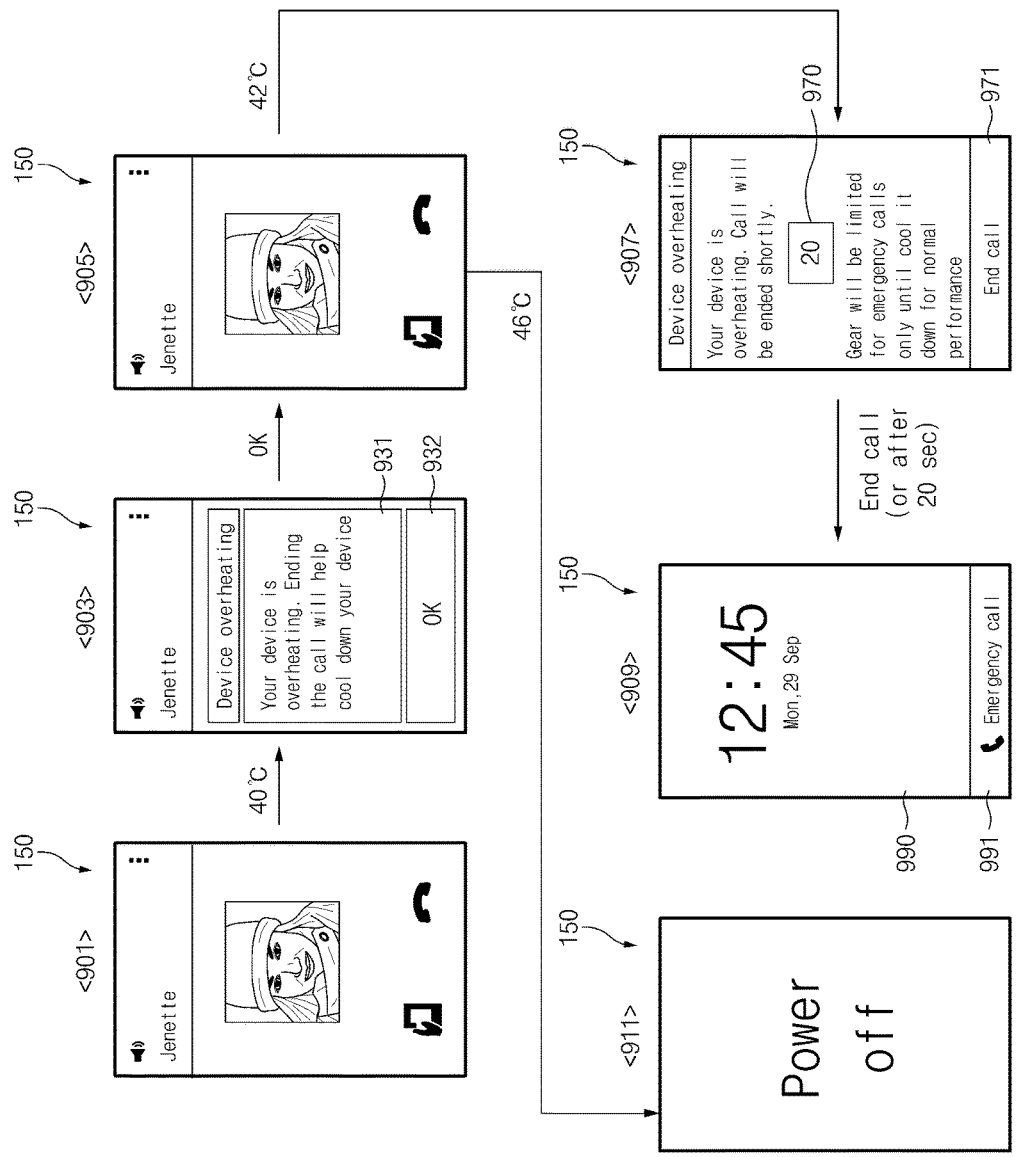
FIG. 9 is a view illustrating a temperature specific function control related screen interface according to various embodiments of the present disclosure.

FIG. 9 is a view illustrating a temperature specific function control related screen interface according to various embodiments of the present disclosure. The screen interfaces of FIG. 9 can be displayed during the method of FIG. 5 as will be described. In correspondence to a call function execution, as shown in a state 901, the electronic device 100 may output a call function execution screen to the display 150. The electronic device 100 may perform a temperature detection (such as during operation 505) in a specific period or in real time during a call function execution. According to an embodiment of the present disclosure, the electronic device 100 may obtain temperature information of the temperature sensor 181 for communication module and perform a comparison with temperature setting information.

When the detected temperature information satisfies a specified constrained temperature condition (for example, 40° C./104° F.) (such as the condition of operation 507) due to a temperature rise, as shown in a state 903, the electronic device 100 may output a function restriction warning message to the display 150. The function restriction warning message may include warning content 931 and a warning message check virtual button 932. When the warning message check virtual button 932 is selected, the electronic device 100 may remove the outputted function restriction warning message. In correspondence to the function restriction warning message removal, as shown in a state 905, the electronic device 100 may output a call function execution screen to the display 150. After the warning message output, the electronic device 100 may perform a temperature detection (such as during operation 515) in a specific period (such as after elapse of the basic communication performance time in operation 511) or in real time. According to various embodiments of the present disclosure, after the function restriction warning message output, the electronic device 100 may process a temperature detection period differently from a temperature detection period before the function restriction warning message output. For example, the electronic device 100 may set a temperature detection period faster after the function restriction warning message output.

When the detected temperature information satisfies a restricted temperature condition (for example, 42° C./107.6° F.) (such as the condition in operation 521) due to a temperature rise, as shown in a state 907, the electronic device 100 may output a cool down warning message relating to cool down processing to the display 150 (such as in operation 523). The cool down warning message, for example, may include timer count information 970 for warning a cool down execution time point and a call end virtual button 971.

When the call end virtual button 971 is selected or the timer driving is completed, as shown in a state 907, the electronic device 100 may output a screen corresponding to cool down processing to the display 150. The cool down processing screen may include a home screen 990 and an emergency call function virtual button 991. The electronic device 100 may not perform screen switching even if an input event occurs as maintaining the home screen 990 in a lock state. When the emergency call function virtual button 991 is selected, the electronic device 100 may attempt a call connection to a specified phone number regardless of the lock of the home screen 990.

According to various embodiments of the present disclosure, when a specified limited temperature condition (such as the condition of operation 517) (for example, more than 46° C./114.8° F.) is satisfied in a state that a communication function is executed, as shown in a state 911, the electronic device 100 may process power off (such as in operation 519). In this case, the electronic device 100 may process a communication function termination and another electronic device transmission of a message relating to a communication function termination. Although it is described above that the state 905 is changed into the state 911, embodiments of the present disclosure are not limited thereto. When the detected temperature information satisfies a limited temperature condition during a process for performing temperature detection, the electronic device 100 may perform power off processing corresponding to the state 911. For example, when a limited temperature condition is satisfied as a temperature of a device rises due to an outside air temperature in a cool down state, as shown in a state 909, the electronic device 100 may process power off. Additionally, when a limited temperature condition is satisfied as a temperature of a device rises in an operation for outputting a warning message, as shown in a state 903, the electronic device 100 may process power off. Additionally, when the detected temperature information satisfies a limited temperature condition during timer driving, the electronic device 100 may perform power off processing in a state 907.

Figure 10:
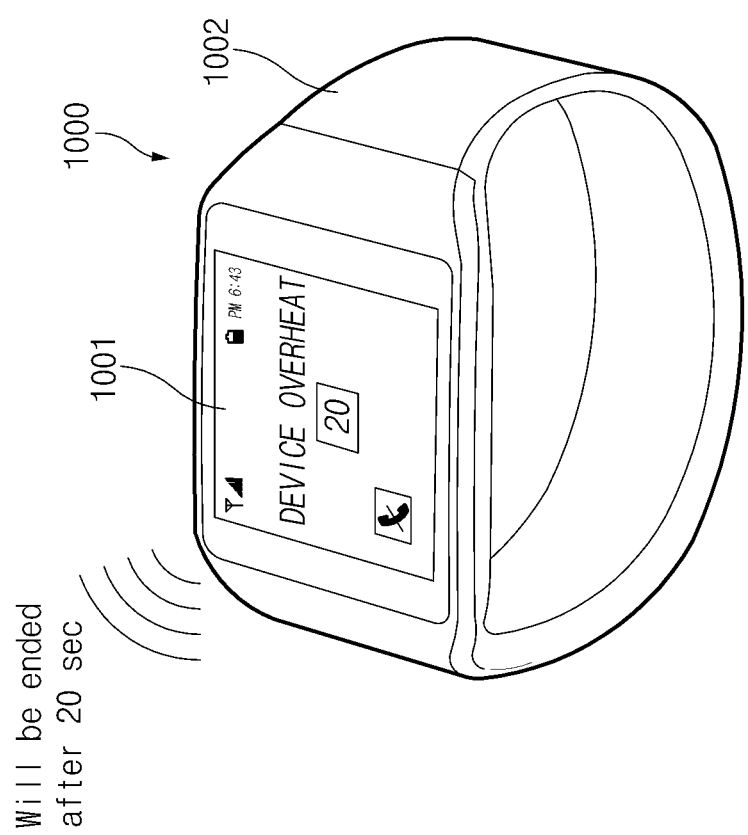
FIG. 10 is a schematic view illustrating an appearance of an electronic device according to various embodiments of the present disclosure.

FIG. 10 is a schematic view illustrating an appearance of an electronic device according to various embodiments of the present disclosure.

The electronic device 1000 may be in a wearable form. In relation to this, the electronic device 1000 may include a device part 1001 and a wearing part 1002. The device part 1001 may include hardware relating to at least one user function support such as a call function, including a display area. The device part 1001, for example, may output a function termination schedule time when it becomes a specified device overheat state due to a temperature rise of a device during call function performance. The function termination schedule time, for example, may represent a termination schedule time point of a call function in execution or may represent a cool down execution time point.

Figure 11:
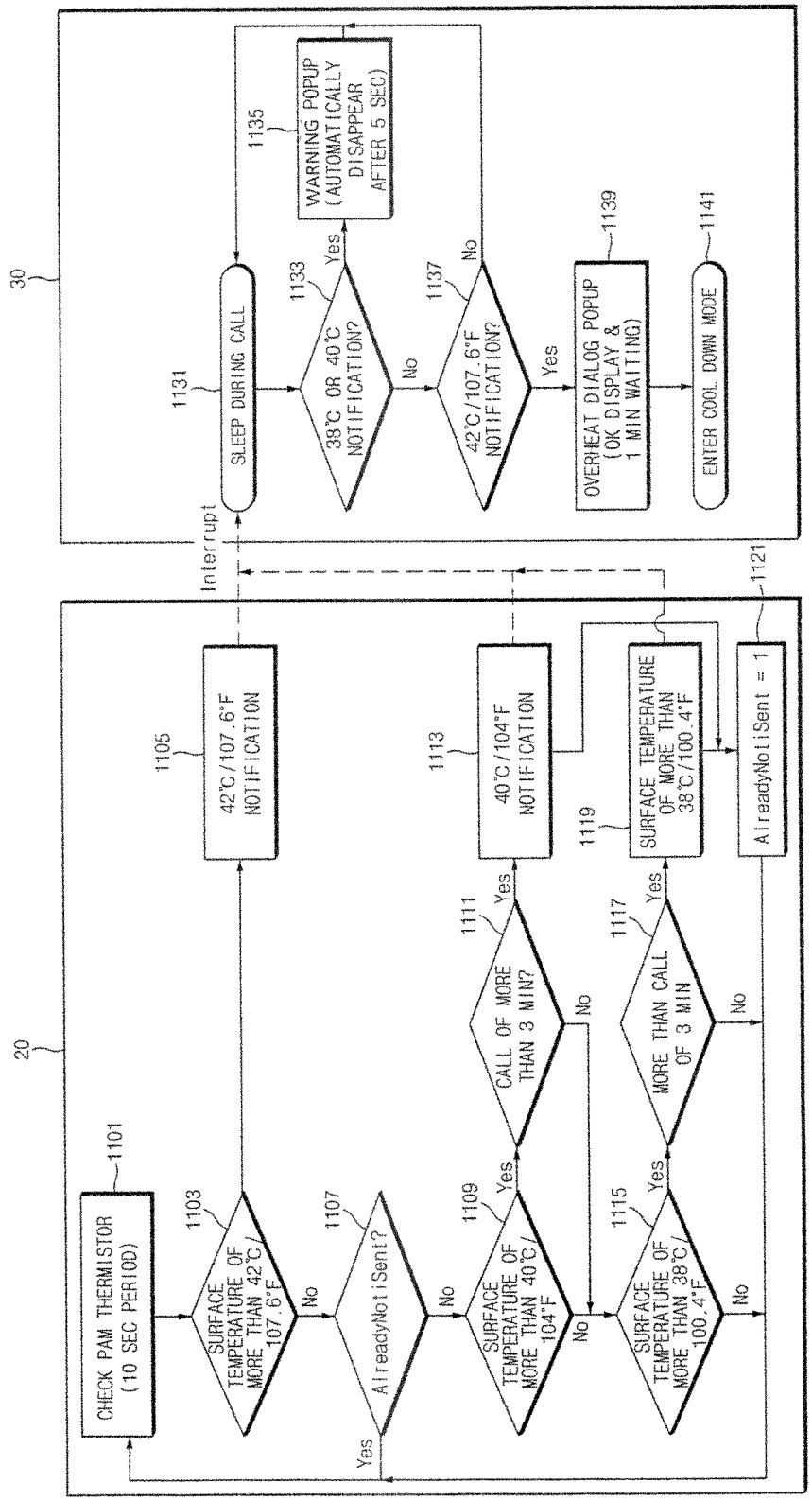
FIG. 11 is a flowchart illustrating a communication function control related processor management according to various embodiments of the present disclosure.

When the electronic device 1000 is a watch type, the wearing part 1002, for example, may be prepared with various types such as a band type, a chain type, and a belt type in order to allow a user to wear the device part 1001 on a wrist. The wearing part 1002 may have various formats according to a wearable form. For example, when the electronic device 1000 is a necklace type, the wearing part 1002 may have a necklace strap form. FIG. 11 is a flowchart illustrating a communication function control related processor management according to various embodiments of the present disclosure. The application processor 30 may have a sleep state during a call in operation 1131. In relation to this, while the application processor 30 shifts into a sleep state, the communication processor 20 receives a call connection request and establishes a call channel.

When a call function is executed, the communication processor 20 may check a PAM Thermistor in operation 1101. For example, the communication processor 20 may check the PAM Thermistor in a specified specific period (for example, a 10 sec period). In operation 1103, the communication processor 20 may check whether the detected temperature information is more than a surface temperature of 42° C./107.6° F. When it is more than the surface temperature of 42° C./107.6° F., the communication processor 20 may perform 42° C./107.6° F. notification in operation 1105. When it is less than the surface temperature of 42° C./107.6° F., the communication processor 20 may check whether a notification for the detected temperature information (AlreadyNotiSent) is performed in operation 1107. When the notification for the detected temperature information is performed, the processor management branches into operation 1101 and re-performs a temperature check corresponding to a specific period.

When the notification for the detected temperature information is not performed, the communication processor 20 may check whether the detected temperature information is more than a surface temperature of 40° C./104° F. in operation 1109. When it is more than the surface temperature of 40° C./104° F., the communication processor 20 may check whether the call function is maintained for more than 3 min in operation 1111. When the call function is maintained for more than the surface temperature of 40° C./104° F., the communication processor 20 may check whether the call function is maintained for more than 3 min in operation 1111. In operation 1109, if it is less than the surface temperature of 40° C./104° F., the communication processor 20 may check whether it is more than a surface temperature of 38° in operation 1115. When it is more than the surface temperature of 38° C., the communication processor 20 may check whether a communication function (for example, a call function) is maintained for more than 3 min in operation 1117. When the communication function is maintained for more than 3 min, the communication processor 20 may perform a 38° C. notification in operation 1119.

In correspondence to performing a temperature information notification detected in operation 1113 or operation 1119, the communication processor 20 may set an AlreadyNotiSent value to 1 in operation 1121. For example, the communication processor 20 may set that a notification for the detected temperature information is performed. After operation 1115, operation 117, and operation 1121, the communication processor 20 may branch into operation 1101 and re-perform subsequent operations. According to various embodiments of the present disclosure, the communication processor 20 may deliver an interrupt for temperature notification to the application processor 30 as performing the detected temperature information notification in operation 1105, operation 1113, and operation 1119.

As described above, the application processor 30 in a sleep state during a call in operation 1131 may check whether the interrupt relates to a 38° C. notification or a 40° C./104° F. notification in operation 1133. When the interrupt relates to a 38° C. notification or a 40° C./104° F. notification is received, the application processor 30 may output a warning popup in operation 1135. The application processor 30 may remove a heat generation state notification popup in correspondence to the elapse of a specific time (for example, after 5 sec). The application processor 30 may branch into operation 1131 and may be shifted into a sleep state during a call.

If the interrupt does not relate to a 38° C. notification or a 40° C./104° F. notification in operation 1133, the application processor 30 may check whether an interrupt relating to a 42° C./107.6° F. notification is received in operation 1137. If the interrupt does not relate to the 42° C./107.6° F. notification, the application processor 30 may branch into operation 1131 and may be shifted into a sleep state.

If the interrupt for the 42° C./107.6° F. notification is received in operation 1137, the application processor 30 may output an overheating dialog popup in operation 1139. The application processor 30 may output an OK virtual key button additionally during the overheating dialog popup output process. The application processor 30 may remove the overheating dialog popup after the OK virtual key button is pressed or waiting for a specific time (for example, 1 min). Then, the application processor 30 may process a cool down mode entry in operation 1141.

Figure 12:
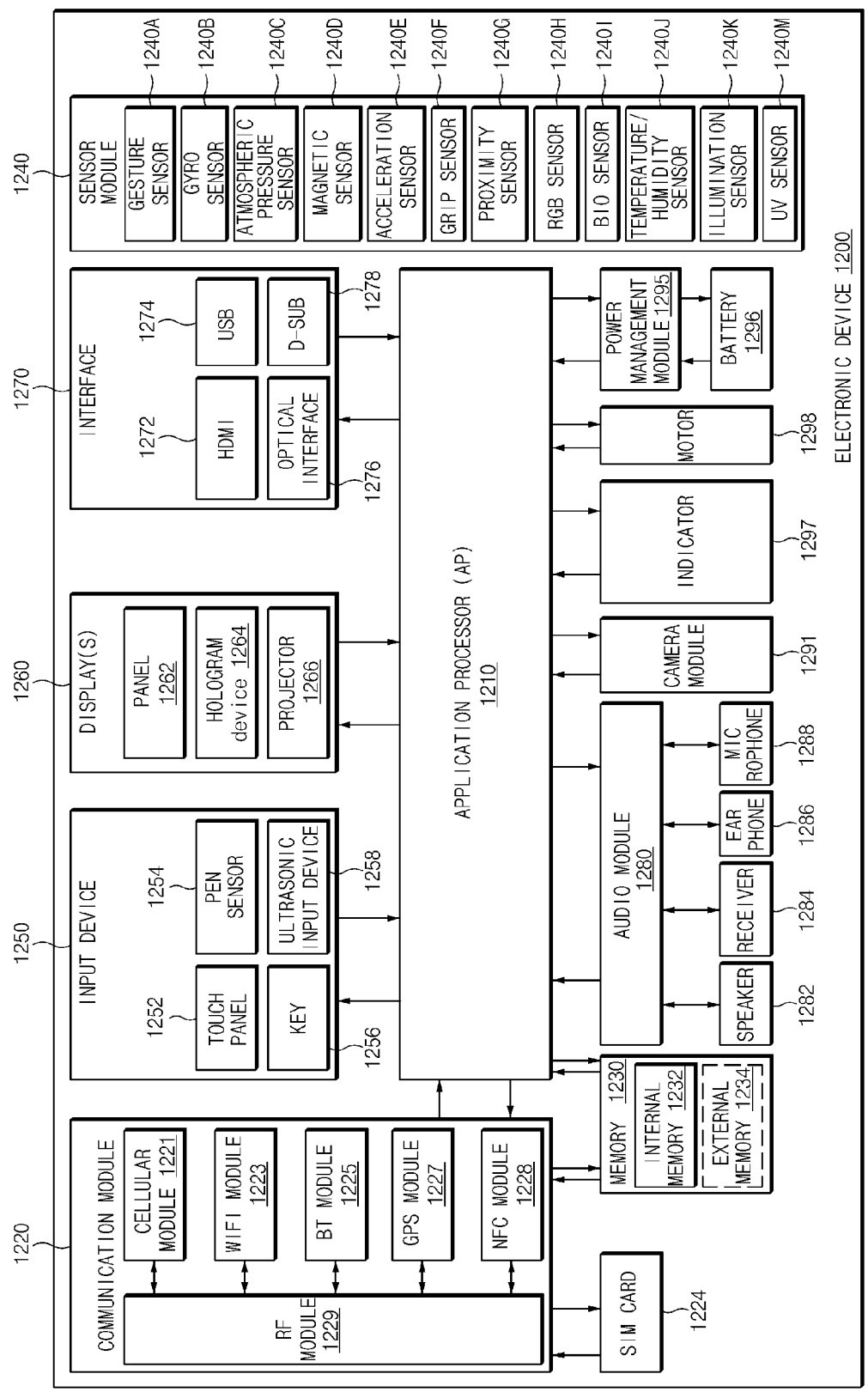
FIG. 12 is a view illustrating an electronic device for supporting a temperature based function control according to various embodiments of the present disclosure.

Referring to FIG. 12, the electronic device 1200, for example, may configure all or part of the above-mentioned electronic device 100 shown in FIG. 1. The electronic device 1200 may include application processor (AP) 1210, a communication module 1220, a subscriber identification module (SIM) card 1224, a memory 1230, a sensor module 1240, an input device 1250, a display 1260, an interface 1270, an audio module 1280, a camera module 1291, a power management module 1295, a battery 1296, an indicator 1297, and a motor 1298.

The AP 1210 may control a plurality of hardware or software components connected to the AP 1210 and also may perform various data processing and operations by executing an operating system or an application program. The AP 1210 may be implemented with a system on chip (SoC), for example. According to an embodiment of the present disclosure, the AP 1210 may further include a graphic processing unit (GPU) (not shown) and/or an image signal processor. The AP 1210 may include at least part (for example, the cellular module 1221) of components shown in FIG. 12. The AP 1210 may load commands or data received from at least one of other components (for example, non-volatile memory) and process them and may store various data in a nonvolatile memory.

The communication module 1220 may have the same or similar configuration to the communication interface 160 of FIG. 1. The communication module 1220 may include a cellular module 1221, a WiFi module 1223, a BT module 1225, a GPS module 1227, an NFC module 1228, and a radio frequency (RF) module 1229.

The cellular module 1221, for example, may provide voice call, video call, text service, or internet service through communication network. According to an embodiment of the present disclosure, the cellular module 1221 may perform a distinction and authentication operation on an electronic device 1200 in a communication network by using a subscriber identification module (for example, the SIM card 1224). According to an embodiment of the present disclosure, the cellular module 1221 may perform at least part of a function that the AP 1210 provides. According to an embodiment of the present disclosure, the cellular module 1221 may further include a communication processor (CP).

Each of the WiFi module 1223, the BT module 1225, the GPS module 1227, and the NFC module 1228 may include a processor for processing data transmitted/received through a corresponding module. According to an embodiment of the present disclosure, at least part (for example, at least one) of the cellular module 1221, the WiFi module 1223, the BT module 1225, the GPS module 1227, and the NFC module 1228 may be included in one integrated chip (IC) or IC package.

The RF module 1229, for example, may transmit/receive communication signals (for example, RF signals). The RF module 1229, for example, may include a transceiver, a power amp module (PAM), a frequency filter, a low noise amplifier (LNA), or an antenna. According to another embodiment of the present disclosure, at least one of the cellular module 1221, the WiFi module 1223, the BT module 1225, the GPS module 1227, and the NFC module 1228 may transmit/receive RF signals through a separate RF module.

The SIM card 1224 may include a card including a SIM and/or an embedded SIM and also may include unique identification information (for example, an integrated circuit card identifier (ICCID)) or subscriber information (for example, an international mobile subscriber identity (IMSI)).

The memory 1230 (for example, the memory 130) may include an internal memory 1232 or an external memory 1234. The internal memory 1232 may include at least one of a volatile memory (for example, dynamic RAM (DRAM), static RAM (SRAM), synchronous dynamic RAM (SDRAM)) and a non-volatile memory (for example, one time programmable ROM (OTPROM), programmable ROM (PROM), erasable and programmable ROM (EPROM), electrically erasable and programmable ROM (EEPROM), mask ROM, flash ROM, NAND flash memory, and NOR flash memory).

The external memory 1234 may further include flash drive, for example, compact flash (CF), secure digital (SD), micro Micro-SD, Mini-SD, extreme digital (xD), or a memory stick. The external memory 1234 may be functionally and/or physically connected to the electronic device 1200 through various interfaces.

The sensor module 1240 measures physical quantities or detects an operating state of the electronic device 1200, thereby converting the measured or detected information into electrical signals. The sensor module 1240 may include at least one of a gesture sensor 1240A, a gyro sensor 1240B, a barometric pressure sensor 1240C, a magnetic sensor 1240D, an acceleration sensor 1240E, a grip sensor 1240F, a proximity sensor 1240G, a color sensor 1240H (for example, a red, green, blue (RGB) sensor), a biometric sensor 1240I, a temperature/humidity sensor 1240J, an illumination sensor 1240K, and an ultra violet (UV) sensor 1240M. Additionally or alternatively, the sensor module 1240 may include an E-nose sensor, an electromyography (EMG) sensor, an electroencephalogram (EEG) sensor, an electrocardiogram (ECG) sensor, an infra red (IR) sensor, an iris sensor, or a fingerprint sensor. The sensor module 1240 may further include a control circuit for controlling at least one sensor therein. According to an embodiment of the present disclosure, the electronic device 1200 may further include a processor configured to control the sensor module 1240 as part of or separately from the AP 1210 and thus may control the sensor module 1240 while the AP 1210 is in a sleep state.

The input device 1250 may include a touch panel 1252, a (digital) pen sensor 1254, a key 1256, or an ultrasonic input device 1258. The touch panel 1252 may use at least one of capacitive, resistive, infrared, or ultrasonic methods, for example. Additionally, the touch panel 1252 may further include a control circuit. The touch panel 1252 may further include a tactile layer to provide tactile response to a user.

The (digital) pen sensor 1254, for example, may include a sheet for recognition as part of a touch panel or a separate sheet for recognition. The key 1256 may include a physical button, an optical key, or a keypad, for example. The ultrasonic input device 1258 may check data by detecting sound waves through a microphone (for example, a microphone 1288) in the electronic device 1200 through an input tool generating ultrasonic signals.

The display 1260 (for example, the display 150) may include a panel 1262, a hologram device 1264, or a projector 1266. The panel 1262 may have the same or similar configuration to the display 150 of FIG. 1. The panel 1262 may be implemented to be flexible, transparent, or wearable, for example. The panel 1262 and the touch panel 1252 may be configured with one module. The hologram 1264 may show three-dimensional images in the air by using the interference of light. The projector 1266 may display an image by projecting light on a screen. The screen, for example, may be placed inside or outside the electronic device 1200. According to an embodiment of the present disclosure, the display 1260 may further include a control circuit for controlling the panel 1262, the hologram device 1264, or the projector 1266.

The interface 1270 may include a high-definition multimedia interface (HDMI) 1272, a universal serial bus (USB) 1274, an optical interface 1276, or a D-subminiature (sub) 1278, for example. The interface 1270, for example, may be included in the communication interface 160 shown in FIG.

1. Additionally or alternately, the interface 1270 may include a mobile high-definition link (MHL) interface, a secure Digital (SD) card/multi-media card (MMC) interface, or an infrared data association (IrDA) standard interface.

The audio module 1280 may convert sound into electrical signals and convert electrical signals into sounds. At least some components of the audio module 1280, for example, may be included in the input/output interface 140 shown in FIG. 1. The audio module 1280 may process sound information inputted/outputted through a speaker 1282, a receiver 1284, an earphone 1286, or a microphone 1288.

The camera module 1291, as a device for capturing a still image and a video, may include at least one image sensor (for example, a front sensor or a rear sensor), a lens (not shown), an image signal processor (ISP) (not shown), or a flash (not shown) (for example, an LED or a xenon lamp).

The power management module 1295 may manage the power of the electronic device 1200. Although not shown in the drawings, the power management module 1295 may include a power management IC (PMIC), a charger IC, or a battery or fuel gauge, for example. The PMIC may have a wired and/or wireless charging method. As the wireless charging method, for example, there is a magnetic resonance method, a magnetic induction method, or an electromagnetic method. An additional circuit for wireless charging, for example, a circuit such as a coil loop, a resonant circuit, or a rectifier circuit, may be added. The battery gauge may measure the remaining amount of the battery 1296, or a voltage, current, or temperature thereof during charging. The battery 1296, for example, may include a rechargeable battery and/or a solar battery.

The indicator 1297 may display a specific state of the electronic device 1200 or part thereof (for example, the AP 1210), for example, a booting state, a message state, or a charging state. The motor 1298 may convert electrical signals into mechanical vibration and may generate vibration or haptic effect. Although not shown in the drawings, the electronic device 1200 may include a processing device (for example, a GPU) for mobile TV support. A processing device for mobile TV support may process media data according to the standards such as digital multimedia broadcasting (DMB), digital video broadcasting (DVB), or MediaFLO.

Each of the above-mentioned components of the electronic device according to various embodiments of the present disclosure may be configured with at least one component and the name of a corresponding component may vary according to the kind of an electronic device. According to various embodiments of the present disclosure, an electronic device according to various embodiments of the present disclosure may include at least one of the above-mentioned components, may not include some of the above-mentioned components, or may further include another component. Additionally, some of components in an electronic device according to various embodiments of the present disclosure are configured as one entity, so that functions of previous corresponding components are performed identically.

Figure 13:
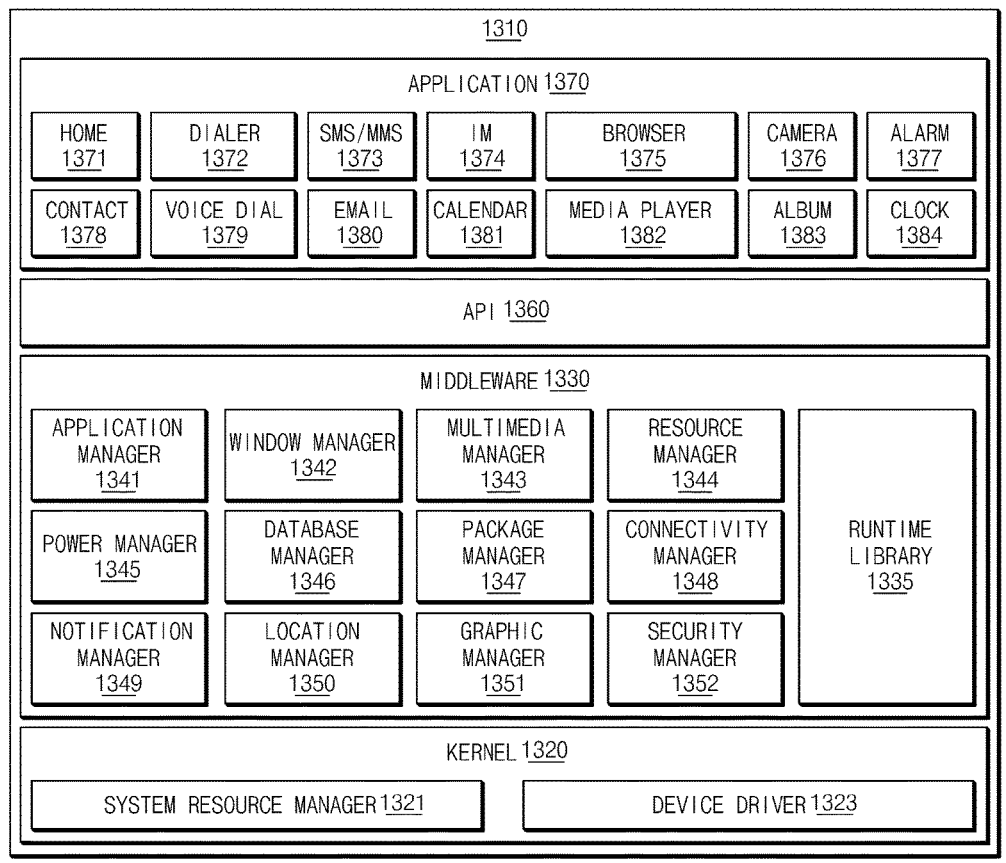
FIG. 13 is a block diagram illustrating a program module according to various embodiments of the present disclosure.

FIG. 13 is a block diagram illustrating a program module according to various embodiments of the present disclosure.

Referring to FIG. 13, according to an embodiment of the present disclosure, the program module 1310 may include an operating system (OS) for controlling a resource relating to an electronic device (for example, the electronic device 100) and/or various applications running on the OS. The OS, for example, may include android, iOS, windows, symbian, tizen, or bada.

The program module 1310 may include an OS and an application 1370. The OS may include a kernel 1320, a middleware 1330, and an API 1360. At least part of the program module 1310 may be preloaded on an electronic device or may be downloaded from a server (for example, 104).

The kernel 1320, for example, may include a system resource manager 1321 or a device driver 1323. The system resource manager 1321 may perform the control, allocation, or retrieval of a system resource. According to an embodiment of the disclosure, the system resource manager 1321 may include a process management unit, a memory management unit, or a file system management unit. The device driver 1323, for example, may include a display driver, a camera driver, a Bluetooth driver, a sharing memory driver, a USB driver, a keypad driver, a WiFi driver, an audio driver, or an inter-process communication (IPC) driver.

The middleware 1330, for example, may provide a function that the application 1330 requires commonly, or may provide various functions to the application 1330 through the API 1360 in order to allow the application 1330 to efficiently use a limited system resource inside the electronic device. According to an embodiment of the disclosure, the middleware 1330 may include at least one of a runtime library 1335, an application manager 1341, a window manager 1342, a multimedia manager 1343, a resource manager 1344, a power manager 1345, a database manager 1346, a package manager 1347, a connectivity manager 1348, a notification manager 1349, a location manager 1350, a graphic manager 1351, and a security manager 1352.

The runtime library 1335, for example, may include a library module that a complier uses to add a new function through a programming language while the application 1330 is running. The runtime library 1335 may perform a function on input/output management, memory management, or an arithmetic function.

The application manager 1341, for example, may mange the life cycle of at least one application among the applications 1370. The window manager 1342 may manage a GUI resource used in a screen. The multimedia manager 1343 may recognize a format for playing various media files and may encode or decode a media file by using the codec corresponding to a corresponding format. The resource manager 1344 may manage a resource such as a source code, a memory, or a storage space of at least any one of the applications 1370.

The power manager 1345, for example, may operate together with a basic input/output system (BIOS) to manage the battery or power and may provide power information necessary for an operation of the electronic device. The database manager 1346 may create, search, or modify a database used in at least one application among the applications 1370. The package manager 1347 may manage the installation or update of an application distributed in a package file format.

The connectivity manger 1348 may manage a wireless connection such as WiFi or Bluetooth. The notification manager 1349 may display or notify an event such as arrival messages, appointments, and proximity alerts. The location manager 1350 may manage location information on an electronic device. The graphic manager 1351 may manage a graphic effect to be provided to a user or a user interface relating thereto. The security manager 1352 may provide various security functions necessary for system security or user authentication. According to an embodiment of the present disclosure, when an electronic device (for example, the electronic device 100) includes a phone function, the middleware 1330 may further include a telephony manager for managing a voice or video call function of the electronic device.

The middleware 1330 may include a middleware module for forming a combination of various functions of the above-mentioned components. The middleware 1330 may provide a module specialized for each type of OS to provide differentiated functions. Additionally, the middleware 1330 may delete part of existing components or add new components dynamically.

The API 1360, for example, as a set of API programming functions, may be provided as another configuration according to OS. For example, in the case of android or iOS, one API set may be provided for each platform and in the case Tizen, at least two API sets may be provided for each platform.

The application 1330 (for example, the application 147) may include at least one application for providing functions such as a home 1371, a dialer 1372, an SMS/MMS 1373, an instant message 1374, a browser 1375, a camera 1376, an alarm 1377, a contact 1378, a voice dial 1379, an e-mail 1380, a calendar 1381, a media player 1382, an album 1383, a clock 1384, health care (for example, measure an exercise amount or blood sugar), or environmental information provision (for example, provide air pressure, humidity, or temperature information).

According to an embodiment of the disclosure, the application 1330 may include an application (hereinafter referred to as "information exchange application") for supporting information exchange between the electronic device (for example, the electronic device 100) and an external electronic device (for example, the electronic device 102). The information exchange application, for example, may include a notification relay application for relaying specific information to the external device or a device management application for managing the external electronic device.

For example, the notification relay application may have a function for relaying to an external electronic device (for example, the electronic device 102) notification information occurring from another application (for example, an SMS/MMS application, an e-mail application, a health care application, or an environmental information application) of the electronic device. Additionally, the notification relay application may receive notification information from an external electronic device and may then provide the received notification information to a user. The device management application, for example, may manage (for example, install, delete, or update) at least one function (turn-on/turn off of the external electronic device itself (or some components) or the brightness (or resolution) adjustment of a display) of an external electronic device (for example, the electronic device 102) communicating with the electronic device, an application operating in the external electronic device, or a service (for example, call service or message service) provided from the external device.

According to an embodiment of the disclosure, the application 1330 may include a specific application (for example, a health care application) according to the property (for example, as the property of an electronic device, when the type of the electronic device is a mobile medical device) of the external electronic device (for example, the electronic device 102). According to an embodiment of the present disclosure, the application 1330 may include an application received from an external electronic device (for example, the server 104 or the electronic device 102). According to an embodiment of the disclosure, the application 1370 may include a preloaded application or a third party application downloadable from a server. The names of components in the program module 1310 according to the shown embodiment may vary depending on the type of OS.

According to various embodiments of the present disclosure, at least part of the program module 1310 may be implemented with software, firmware, hardware, or a combination thereof. At least part of the programming module 1310, for example, may be implemented (for example, executed) by a processor (for example, the AP 1210). At least part of the programming module 1310 may include a module, a program, a routine, sets of instructions, or a process to perform at least one function, for example.

According to various embodiments of the present disclosure, hardware failures or user damages (for example, discomfort and low-temperature burn) may be prevented by restricting functions corresponding to heat generation.

The term "module" used in various embodiments of the present disclosure, for example, may mean a unit including a combination of at least one of hardware, software, and firmware. The term "module" and the term "unit", "logic", "logical block", "component", or "circuit" may be interchangeably used. A "module" may be a minimum unit or part of an integrally configured component. A "module" may be a minimum unit performing at least one function or part thereof. A "module" may be implemented mechanically or electronically. For example, "module" according to various embodiments of the present disclosure may include at least one of an application-specific integrated circuit (ASIC) chip performing certain operations, field-programmable gate arrays (FPGAs), or a programmable-logic device, all of which are known or to be developed in the future.

According to various embodiments of the present disclosure, at least part of a device (for example, modules or functions thereof) or a method (for example, operations) according to this disclosure, for example, as in a form of a programming module, may be implemented using an instruction stored in computer-readable storage media. When at least one processor (for example, the processor 120) executes an instruction, it may perform a function corresponding to the instruction. The non-transitory computer-readable storage media may include the memory 130, for example.

The non-transitory computer-readable storage media may include hard disks, floppy disks, magnetic media (for example, magnetic tape), optical media (for example, CD-ROM, and DVD), magneto-optical media (for example, floptical disk), and hardware devices (for example, ROM, RAM, or flash memory). Additionally, a program instruction may include high-level language code executable by a computer using an interpreter in addition to machine code created by a complier. The hardware device may be configured to operate as at least one software module to perform an operation of various embodiments of the present disclosure and vice versa.

According to the above-mentioned various embodiments of the present disclosure, computer readable recording media may store at least one instruction executed by at least one processor and the at least one instruction may include performing a temperature detection corresponding to a communication function execution, driving a timer for warning the communication function termination when temperature information detected corresponding to the temperature detection satisfies a specified temperature condition, and outputting count information corresponding to the timer driving.

A module or a programming module according to various embodiments of the present disclosure may include at least one of the above-mentioned components, may not include some of the above-mentioned components, or may further include another component. Operations performed by a module, a programming module, or other components according to various embodiments of the present disclosure may be executed through a sequential, parallel, repetitive or heuristic method. Additionally, some operations may be executed in a different order or may be omitted. Or, other operations may be added.

Moreover, the embodiments disclosed in this specification are suggested for the description and understanding of technical content but do not limit the range of the present disclosure. Accordingly, the range of the present disclosure should be interpreted as including all modifications or various other embodiments based on the technical idea of the present disclosure.

What is claimed is:

1. An electronic device comprising:
a communication interface configured to support a communication function; and
one or more processors configured to perform a temperature detection of the electronic device during a communication function execution, drive a timer, warn of a communication function termination if a detected temperature satisfies a specified temperature condition, and output count information corresponding to the timer driving.

2. The electronic device of claim 1, wherein the one or more processors is configured to maintain the communication function execution during a specific basic communication performance time before the temperature detection performance.

3. The electronic device of claim 1, wherein the one or more processors is configured to maintain the communication function execution for a specific basic communication performance time when the detected temperature satisfies the specified temperature condition.

4. The electronic device of claim 3, wherein the one or more processors is configured to drive the timer and output count information corresponding to the timer driving when performing a temperature redetection after the specific basic communication performance time elapses and a redetected temperature satisfies the specified temperature condition.

5. The electronic device of claim 1, wherein the one or more processors is configured to output at least one of display data and audio data corresponding to the count information.

6. The electronic device of claim 1, wherein the one or more processors is configured to output a first virtual key button configured to maintain the communication function for the timer driving time, a second virtual key button configured to terminate the communication function, and a third virtual key button configured to delay the communication function termination corresponding to the timer driving for a specific time.

7. The electronic device of claim 1, wherein the one or more processors is configured to not to reuse the communication function for a specific time when the timer driving expires.

8. The electronic device of claim 7, wherein the one or more processors is configured to output information relating to a communication function reuse availability when the specific time elapses.

9. The electronic device of aim 1, wherein the one or more processors is configured to power off by cutting power supply when the timer driving expires or power off by cutting power supply when a re-performed temperature detection result satisfies the specified limited temperature condition after the timer driving expires.

10. The electronic device of claim 1, wherein the one or more processors is configured to transmit to another electronic device at least one of a communication function termination schedule time corresponding to the timer driving and the communication function termination.

11. A function controlling method of an electronic device, the method comprising:
performing a temperature detection of the electronic device corresponding to a communication function execution;
driving a timer to warn of a communication function termination if the detected temperature information satisfies a specified temperature condition; and
outputting count information corresponding to the timer driving.

12. The method of claim 11, further comprising maintaining the communication function execution during a specific basic communication performance time before the temperature detection performance.

13. The method of claim 11, further comprising maintaining the communication function execution for a specific basic communication performance time when the detected temperature satisfies the specified temperature condition after the temperature detection.

14. The method of claim 13, wherein the driving of the timer comprises, when performing a temperature redetection after the specific basic communication performance time elapses and then driving the timer when redetected temperature information satisfies the specified temperature condition.

15. The method of claim 11, wherein the outputting of the count information comprises at least one of outputting display data corresponding to the count information and outputting audio data corresponding to the count information.

16. The method of claim 11, wherein the outputting of the count information comprises outputting a first virtual key button configured to maintain a communication function for the timer driving time, a second virtual key button configured to terminate the communication function, and a third virtual key button configured to delay a communication function termination corresponding to the timer driving for a specific time.

17. The method of claim 11, further comprising preventing reusing the communication function for a specific time when the timer driving expires.

18. The method of claim 17, further outputting information relating to a communication function reuse availability when the specific time elapses.

19. The method of claim 11, further comprising performing power off by cutting power supply when the timer driving expires.

20. The method of claim 11, further comprising transmitting to another electronic device at least one of a communication function termination schedule time corresponding to the timer driving and the communication function termination.

21. An electronic device comprising:
a processor comprising:
a communication processor configured to detect a temperature, and establish a phone call; and
an application processor configured to perform one of cause the electronic device to enter a cool down mode, or issue a warning message in response to at least one particular interrupt from the communication processor: and wherein communication processor sends the at least one particular interrupt to the application processor, responsive to detecting the temperature exceeds one or more thresholds.

22. The electronic device of claim 21, wherein the at least one pat ular interrupt includes a first interrupt and a second interrupt, and wherein the one or more threshold includes a first threshold and a second threshold, and wherein the communication processor sends the first interrupt if the temperature exceeds the first threshold, and wherein the application processor issues a warning message responsive to receiving the first interrupt, and wherein the communication processor sends the second interrupt if the temperature exceeds the second threshold, and wherein the application processor places the electronic device in a cool down mode responsive to receiving the second interrupt.

23. The electronic device of claim 21, wherein issuing the warning message further comprises ending the phone call established by the communication processor after a specific period of time.

24. The electronic device of claim 23, wherein placing the electronic device in cool down mode comprises ending the phone call established by the communication processor.

* * * * *